(12) United States Patent
Kamon

(10) Patent No.: US 11,272,830 B2
(45) Date of Patent: Mar. 15, 2022

(54) ENDOSCOPE SYSTEM AND OPERATION METHOD THEREFOR

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

(21) Appl. No.: 16/575,924

(22) Filed: Sep. 19, 2019

(65) Prior Publication Data

US 2020/0008653 A1 Jan. 9, 2020

Related U.S. Application Data

(63) Continuation of application No. PCT/JP2018/005690, filed on Feb. 19, 2018.

(30) Foreign Application Priority Data

Mar. 30, 2017 (JP) .............................. JP2017-068040

(51) Int. Cl.
*A61B 1/00* (2006.01)
*G06T 7/70* (2017.01)
(Continued)

(52) U.S. Cl.
CPC ...... *A61B 1/00055* (2013.01); *A61B 1/00147* (2013.01); *A61B 5/7221* (2013.01);
(Continued)

(58) Field of Classification Search
CPC ............ A61B 1/00009; A61B 1/00055; A61B 1/00147; A61B 5/7221; G06K 9/2054;
(Continued)

(56) References Cited

U.S. PATENT DOCUMENTS

2002/0188174 A1 12/2002 Aizawa et al.
2008/0009714 A1 1/2008 Oda
(Continued)

FOREIGN PATENT DOCUMENTS

CN 102665526 A 9/2012
CN 106163371 A 11/2016
(Continued)

OTHER PUBLICATIONS

Extended European Search Report dated Mar. 23, 2020, for corresponding European Application No. 18778215.6.
(Continued)

*Primary Examiner* — Brenda C Bernardi
(74) *Attorney, Agent, or Firm* — Birch, Stewart, Kolasch & Birch, LLP

(57) ABSTRACT

Provided is an endoscope system capable of easily re-searching for a detected region of interest, and an operation method for the endoscope system. An endoscope system 10 includes an endoscopic image acquisition unit 54, a region-of-interest detecting unit 80, a position information acquisition unit 81, and a display unit 18. The endoscopic image acquisition unit 54 acquires an endoscopic image acquired by capturing an image of a lumen with an endoscope 12. The region-of-interest detecting unit 80 detects a region of interest in the lumen by using the endoscopic image. The position information acquisition unit 81 acquires position information of the region of interest detected by the region-of-interest detecting unit 80. The display unit 18 displays the position information of the region of interest.

19 Claims, 17 Drawing Sheets

(51) Int. Cl.
*A61B 5/00* (2006.01)
*G06K 9/20* (2006.01)
*G06T 7/00* (2017.01)
*G06V 10/22* (2022.01)

(52) U.S. Cl.
CPC .............. *G06T 7/0012* (2013.01); *G06T 7/70* (2017.01); *G06T 2207/10068* (2013.01); *G06T 2207/30096* (2013.01); *G06V 10/22* (2022.01); *G06V 2201/03* (2022.01)

(58) Field of Classification Search
CPC ...... G06K 2209/05; G02B 23/24; G06T 7/70; G06T 7/0012; G06T 2207/30096; G06T 2207/10068
See application file for complete search history.

(56) References Cited

U.S. PATENT DOCUMENTS

| | | |
|---|---|---|
| 2010/0061597 A1 | 3/2010 | Kanda et al. |
| 2011/0242301 A1 | 10/2011 | Morita |
| 2012/0116158 A1 | 5/2012 | Hale et al. |
| 2012/0220840 A1* | 8/2012 | Morita ................ A61B 1/0638 600/317 |
| 2012/0245415 A1 | 9/2012 | Emura et al. |
| 2014/0230562 A1 | 8/2014 | Yamamoto et al. |
| 2015/0042643 A1* | 2/2015 | Shibata ................ A61B 6/022 345/419 |
| 2015/0181185 A1 | 6/2015 | Ikemoto et al. |
| 2017/0014017 A1 | 1/2017 | Obara et al. |
| 2019/0069757 A1* | 3/2019 | Iwaki ................... A61B 1/0005 |
| 2019/0087959 A1* | 3/2019 | Kitamura ................ G06T 7/90 |

FOREIGN PATENT DOCUMENTS

| | | | |
|---|---|---|---|
| EP | 2 163 183 A1 | | 3/2010 |
| JP | 2000-83889 A | | 3/2000 |
| JP | 2007-330348 A | | 12/2007 |
| JP | 2011-36600 A | | 2/2011 |
| JP | 2011-104016 A | | 6/2011 |
| JP | 2011-206251 A | | 10/2011 |
| JP | 2012-24518 A | | 2/2012 |
| JP | 2013-94337 A | | 5/2013 |
| JP | 2014-18333 A | | 2/2014 |
| JP | 2014-527837 A | | 10/2014 |
| JP | 2014-230612 A | | 12/2014 |
| JP | 2014230612 A | * | 12/2014 |
| JP | 2015-112429 A | | 6/2015 |
| JP | 2015112429 A | * | 6/2015 |
| JP | 2016-21216 A | | 2/2016 |
| JP | 2016021216 A | * | 2/2016 |

OTHER PUBLICATIONS

Japanese Office Action dated Mar. 31, 2020, for corresponding Japanese Application No. 2019508755, with English translation.
Onnoyama et al., "Colon (colorectal)", Clinical Surgery, vol. 13, No. 66, Dec. 2011 pp. 1614-1618.
Tominaga et al., "Basic Manual of Observation by Normal Observation", Digestive Endoscope, vol. 22, No. 4, 2010, pp. 611-615.
International Preliminary Report on Patentability and Written Opinion of the International Searching Authority (forms PCT/IB/373, PCT/ISA/237 and PCT/IB/326), dated Oct. 10, 2019, for corresponding International Application No. PCT/JP2018/005690, with an English translation of the Written Opinion.
International Search Report (form PCT/ISA/210), dated Mar. 27, 2018, for corresponding International Application No. PCT/JP2018/005690, with an English translation.
Chinese Office Action and Search Report, dated Apr. 6, 2021, for corresponding Chinese Application No. 201880020745.0, with an English translation of the Chinese Office Action.
Chinese Office Action for corresponding Chinese Application No. 201880020745.0, dated Nov. 8, 2021, with an English translation.

* cited by examiner

ENDOSCOPE SYSTEM AND OPERATION METHOD THEREFOR

CROSS-REFERENCE TO RELATED APPLICATIONS

This application is a Continuation of PCT International Application No. PCT/JP2018/005690 filed on Feb. 19, 2018, which claims priority under 35 U.S.C. § 119(a) to Japanese Patent Application No. 2017-068040 filed on Mar. 30, 2017. Each of the above application(s) is hereby expressly incorporated by reference, in its entirety, into the present application.

BACKGROUND OF THE INVENTION

1. Field of the Invention

The present invention relates to an endoscope system and an operation method for the endoscope system.

2. Description of the Related Art

In the medical field, diagnoses using an endoscope system including a light source device, an endoscope, and a processor device have widely been performed. In the endoscope system, in a state where the endoscope has been inserted into a subject, the light source device emits illumination light, which is output from the distal end of the endoscope, the endoscope captures an image of an illuminated inside of the subject and outputs image signals, the processor device generates an endoscopic image by using the image signals, and a display unit displays the endoscopic image. Accordingly, a medical practitioner is able to make a diagnosis while viewing the endoscopic image.

When making an endoscopic diagnosis, a medical practitioner attempts to constantly detect all predetermined regions of interest (ROIs) that are to be carefully observed, such as a lesion or benign tumor in an organ. However, the accuracy of detecting the ROIs is influenced by the experiences and skills of the medical practitioner and is also influenced by the degree of fatigue of the medical practitioner. Thus, to reduce variation in diagnostic accuracy among medical practitioners, a technique has been developed for analyzing, using a computer, a large amount of endoscopic data acquired in daily diagnoses and extracting information helpful in diagnoses. For example, an automatic detection function of automatically detecting a ROI by a computer instead of a medical practitioner at an endoscopic diagnosis makes it possible to prevent a ROI from being overlooked by the medical practitioner, and is thus expected to increase the accuracy of an endoscopic diagnosis.

JP2011-036600A describes a technique of generating a virtual endoscopic image by using a computed tomography (CT) image generated by a diagnostic imaging apparatus, such as a CT apparatus, and detecting a ROI from the virtual endoscopic image. In JP2011-036600A, a region that has not yet been presented to a user, such as a medical practitioner, is detected as a ROI. In JP2011-036600A, an outer-shape image of a lumen is generated by using a CT image, and a ROI is displayed at a corresponding position on the outer-shape image in a superimposed manner.

JP2012-024518A describes a technique of automatically detecting a ROI, such as a lesion portion, by using a virtual endoscopic image generated by using a CT image.

SUMMARY OF THE INVENTION

In an endoscopic diagnosis, a ROI may be detected in a forward-direction observation, and the ROI may be carefully examined or treated in a backward-direction observation. In the backward-direction observation in the diagnosis, the position information of the detected ROI can be used for a re-search, but such a system does not exist at present. In some cases, a medical practitioner in a facility gives a diagnosis to a patient referred from another facility, such as another clinic. In such a case, different medical practitioners make diagnoses, and thus the position information of the detected ROI is useful in a re-search. In JP2011-036600A and JP2012-024518A, a ROI is detected by using a CT image. The position information of the detected ROI is useful also in the case of re-searching for the detected ROI in an endoscopic diagnosis.

An object of the present invention is to provide an endoscope system capable of easily re-searching for a detected ROI, and an operation method for the endoscope system.

An endoscope system according to the present invention includes an endoscope, an endoscopic image acquisition unit, a region-of-interest detecting unit, a position information acquisition unit, and a display unit. The endoscopic image acquisition unit acquires an endoscopic image acquired by capturing an image of a lumen with the endoscope. The region-of-interest detecting unit detects a region of interest in the lumen by using the endoscopic image. The position information acquisition unit acquires position information of the region of interest. The display unit that displays the position information of the region of interest.

The lumen may be divided into a plurality of lumen portions, the position information of the region of interest may be lumen portion information of a lumen portion in which the region of interest has been detected among the plurality of lumen portions, and the display unit may display the lumen portion information as the position information of the region of interest.

The position information of the region of interest may be distance information indicating a distance from a reference structure in the lumen, and the display unit may display the distance information as the position information of the region of interest.

The endoscope system may include an insertion length acquisition unit that acquires one or more insertion lengths of an insertion section of the endoscope in the lumen, and the display unit may display, as the position information of the region of interest, an insertion length with which the region of interest has been detected among the one or more insertion lengths.

The endoscope system may include a first marked image generating unit that generates a first marked image having a marking at a position corresponding to the position information of the region of interest in a schematic diagram of the lumen, and the display unit may display the first marked image.

Preferably, the endoscope system may include an insertion state acquisition unit that acquires an insertion state of the endoscope that is in the lumen, and the display unit may display the insertion state of the endoscope at a corresponding position of the schematic diagram.

Preferably, the endoscope system may include a discrimination unit that performs discrimination on the region of interest. Preferably, the discrimination unit may output a discrimination result at least indicating whether the region of interest is a lesion portion or a normal portion. Preferably, the discrimination result may further indicate a type of lesion portion. Preferably, the discrimination result may further indicate confidence in the discrimination result.

Preferably, the endoscope system may include a discrimination result storage unit that stores the discrimination result.

Preferably, the display unit may change a display mode of the marking in accordance with a discrimination result acquired by the discrimination unit.

Preferably, the endoscope system may include a warning unit that provides a warning, based on the position information of the region of interest and the insertion state of the endoscope. Preferably, the warning unit may change a warning mode in accordance with a discrimination result acquired by the discrimination unit.

Preferably, the endoscope system may include a biological feature value calculating unit that calculates a biological feature value of the region of interest, and the display unit may change a display mode of the marking by using the biological feature value in addition to a discrimination result acquired by the discrimination unit.

Preferably, the endoscope system may include a region-of-interest position information storage unit that stores the position information of the region of interest.

The endoscope system may include a shape-of-inserted-endoscope information acquisition unit that acquires shape information of an insertion section of the endoscope that is in the lumen; and a second marked image generating unit that acquires a shape-of-inserted-endoscope image by performing image processing using the shape information of the insertion section and that generates a second marked image having a marking at a position corresponding to the position information of the region of interest in the shape-of-inserted-endoscope image, and the display unit may display the second marked image.

An operation method for an endoscope system according to the present invention includes a step of acquiring, with an endoscopic image acquisition unit, an endoscopic image acquired by capturing an image of a lumen with an endoscope; a step of detecting, with a region-of-interest detecting unit, a region of interest in the lumen by using the endoscopic image; a step of acquiring, with a position information acquisition unit, position information of the region of interest; and a step of displaying, with a display unit, the position information of the region of interest.

With an endoscope system and an operation method for the endoscope system according to the present invention, a detected ROI can be easily re-searched for.

DESCRIPTION OF THE PREFERRED EMBODIMENTS

First Embodiment

Figure 1:
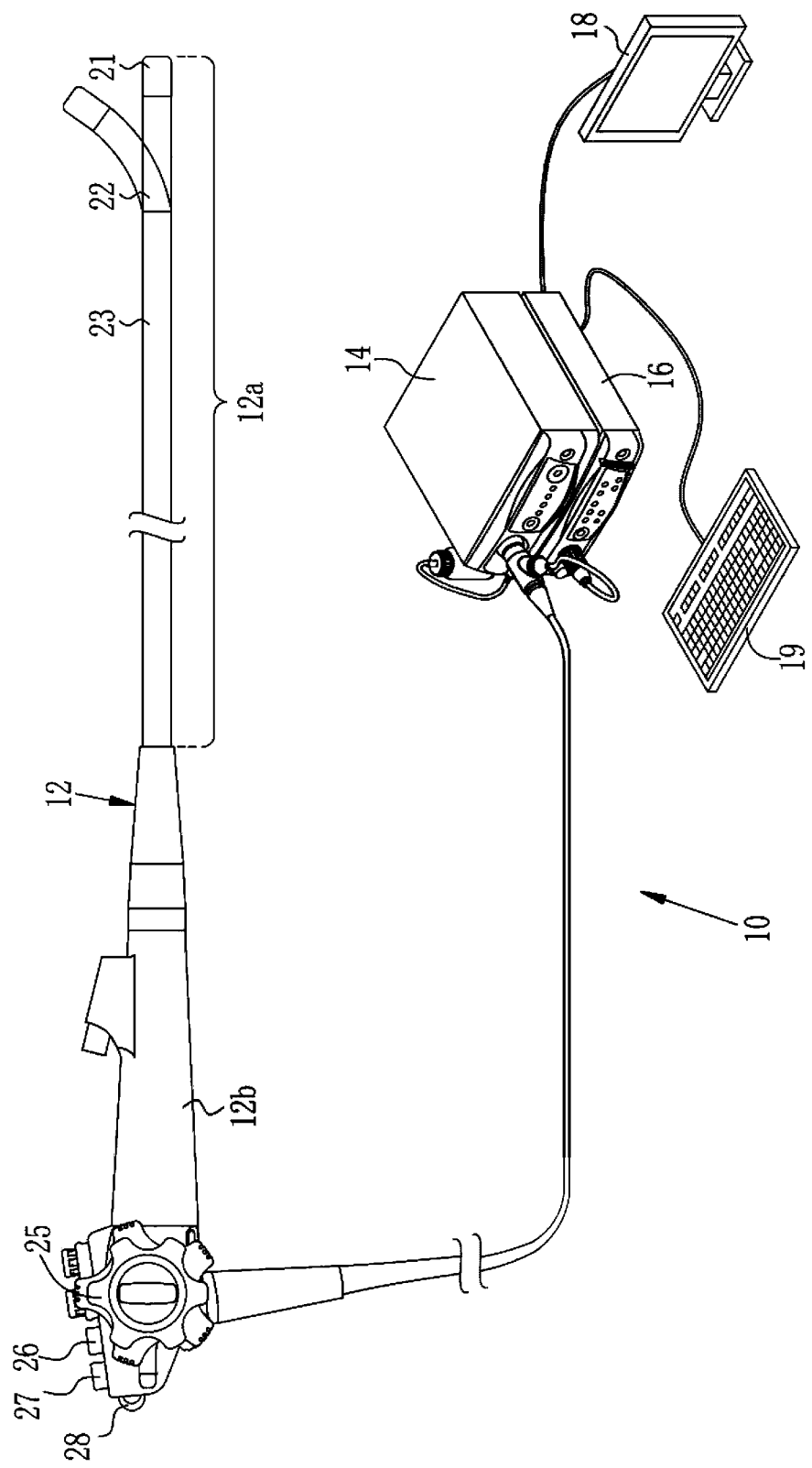
FIG. 1 is an external appearance view of an endoscope system according to a first embodiment.

As illustrated in FIG. 1, an endoscope system 10 has an endoscope 12, a light source device 14, a processor device 16, a display unit 18, and an instruction input unit 19. The endoscope 12 captures an image of a lumen of a living body as a subject. The light source device 14 supplies illumination light for illuminating the lumen to the endoscope 12. The processor device 16 performs predetermined image processing on an endoscopic image acquired through image capturing by the endoscope 12, thereby generating a display image. The display unit 18 is a monitor that displays the display image and information or the like accompanying the display image. The instruction input unit 19 is a console formed of a keyboard, a mouse, and the like, and functions as a user interface that receives an input operation for functional setting or the like. The display unit 18 and the instruction input unit 19 are electrically connected to the processor device 16.

The endoscope 12 is optically connected to the light source device 14 and is electrically connected to the processor device 16. The endoscope 12 has an insertion section 12a and an operation section 12b.

The insertion section 12a is a section to be inserted into a lumen. The insertion section 12a has a distal end portion 21, a bending portion 22, and a flexible pipe portion 23, which are coupled in this order from the distal end side. The distal end portion 21 has, at its distal end surface, an illumination window, an observation window, an air/water supply nozzle, and a forceps outlet, which are not illustrated. The illumination window is used to apply illumination light onto a portion to be observed. The observation window is used to capture light from the portion to be observed. The air/water supply nozzle is used to clean the illumination window and the observation window. The forceps outlet is used to perform various types of treatments by using surgical instruments, such as forceps and an electric scalpel. The bending portion 22 is formed of a plurality of bending pieces coupled to each other and is bent in upward, downward, rightward, and leftward directions. The flexible pipe portion 23 is flexible and can be inserted into a winding tract of the esophagus, intestine, or the like.

The operation section 12b has an angle knob 25, an image storage operation unit 26, a mode switching unit 27, and a zoom operation unit 28. The angle knob 25 is used to cause the bending portion 22 to bend and cause the distal end portion 21 to be directed in a desired direction. The image storage operation unit 26 is used in an operation of storing a still image and/or a moving image in storage (not illustrated). The mode switching unit 27 is used in an operation of switching an observation mode. The zoom operation unit 28 is used in an operation of changing a zoom magnification.

The endoscope system 10 has a normal mode, a special mode, and a region of interest (ROI) search mode as observation modes. In the normal mode, a natural-color image of a lumen (hereinafter referred to as a normal image) is acquired. In the special mode, an image in which at least blood vessels in a lumen are emphasized (hereinafter referred to as a special image) is acquired. In the ROI search mode, although the details will be described below, a ROI in a lumen is detected, and the position information of the detected ROI is displayed on the display unit 18.

Figure 2:
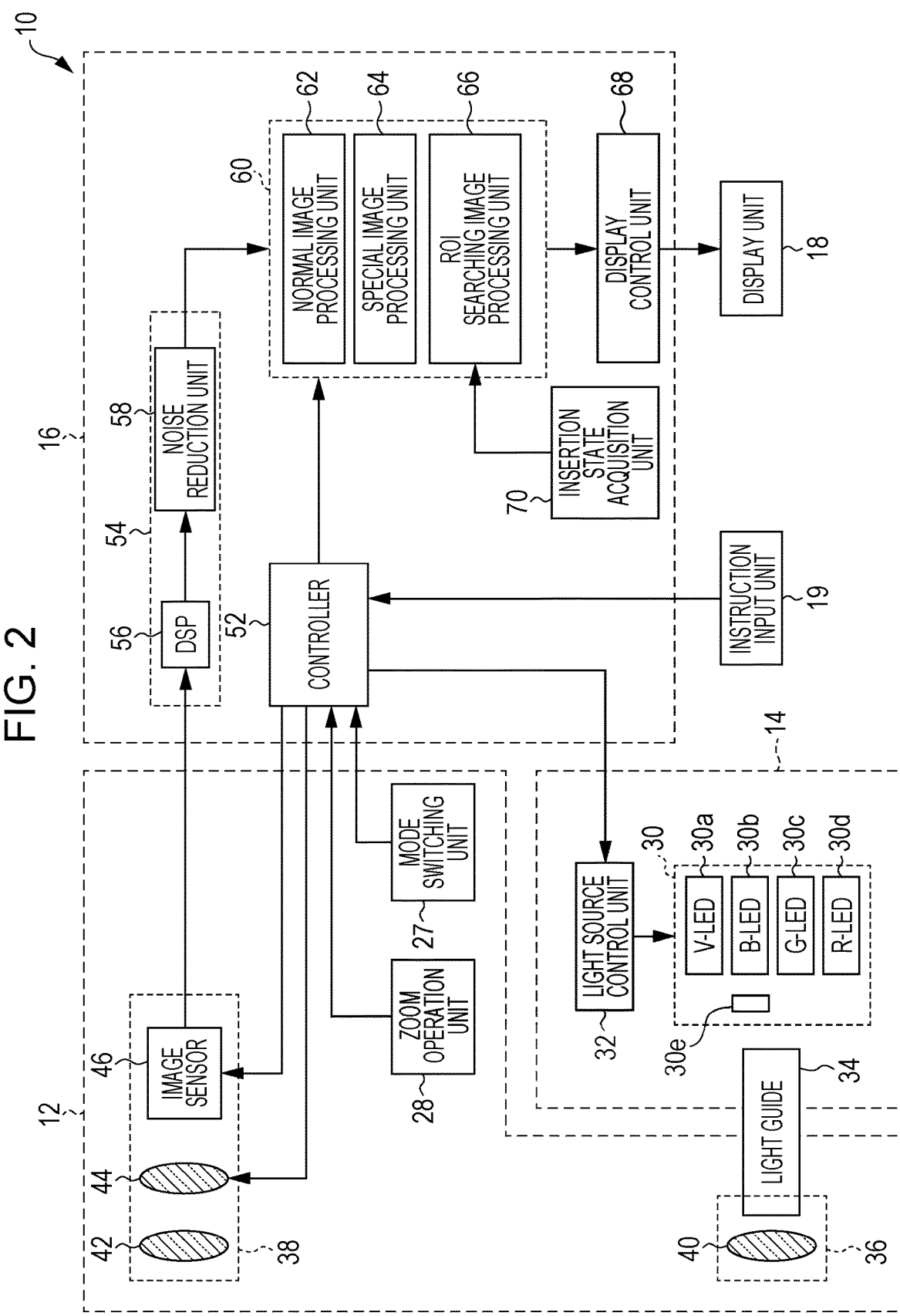
FIG. 2 is a block diagram illustrating the functions of the endoscope system.

As illustrated in FIG. 2, the light source device 14 includes a light source unit 30 that emits illumination light, and a light source control unit 32 that controls the light source unit 30. In this embodiment, the light source unit 30 has semiconductor light sources of a plurality of colors in different wavelength ranges. The semiconductor light sources may be light emitting diodes (LEDs) or the like.

In this embodiment, the light source unit 30 has LEDs of four colors: a violet light emitting diode (V-LED) 30a; a blue light emitting diode (B-LED) 30b; a green light emitting diode (G-LED) 30c; and a red light emitting diode (R-LED) 30d, and an optical filter 30e.

Figure 3:
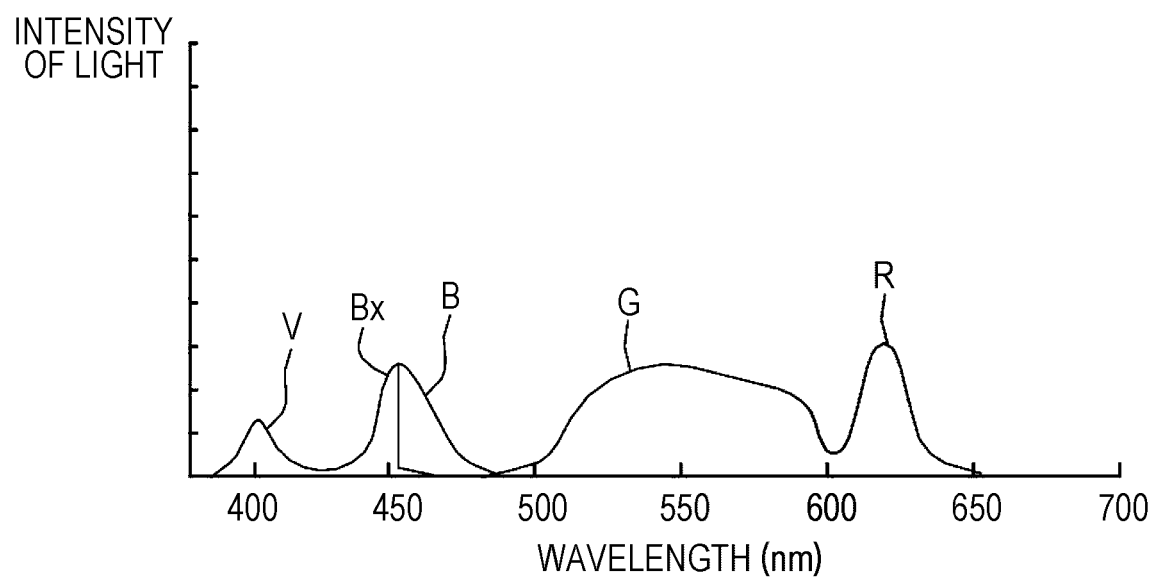
FIG. 3 is a graph illustrating a spectrum of violet light V, blue light B, blue light Bx, green light G, and red light R.

As illustrated in FIG. 3, the V-LED 30a emits violet light V in a wavelength range of 380 nm to 420 nm. The B-LED 30b emits blue light B in a wavelength range of 420 nm to 500 nm. The G-LED 30c emits green light G in a wavelength range of 480 nm to 600 nm. The R-LED 30d emits red light R in a wavelength range of 600 nm to 650 nm. The light of each color may have a center wavelength and a peak wavelength that are identical to or different from each other.

The optical filter 30e adjusts the wavelength range of light emitted by an LED. In this embodiment, the optical filter 30e is disposed on the light path of the B-LED 30b and passes a short-wavelength component in the wavelength range of the B-LED 30b. A long-wavelength component in the wavelength range of the B-LED 30b is regarded as a factor in reducing the contrast between mucous membranes and blood vessels, and thus it is preferable to supply a short-wavelength component in the wavelength range of the B-LED 30b to a light guide 34, which will be described below. In this embodiment, the optical filter 30e passes light of 450 nm or less in the wavelength range of the B-LED 30b, thereby generating blue light Bx in a wavelength range of 420 nm to 450 nm. The disposition of the optical filter 30e, which is disposed on the light path of the B-LED 30b in this embodiment, is not limited thereto. For example, the optical filter 30e may be disposed on the light path of the G-LED 30c. The wavelength component that the optical filter 30e passes can be set appropriately. For example, in a case where the optical filter 30e is disposed on the light path of the G-LED 30c, the optical filter 30e passes part of the wavelength range of the G-LED 30c.

The light source control unit 32 controls ON and OFF of each of the LEDs 30a to 30d, the balance (hereinafter referred to as a light amount ratio) of the amounts of light emitted by the individual LEDs 30a to 30d, and the like independently from each other, thereby adjusting the emission timing, emission period, amount of light, and spectrum of illumination light. In addition, the light source control unit 32 controls the wavelength range of illumination light by changing the optical filter 30e. In this embodiment, the light source control unit 32 adjusts the current and voltage for driving the LEDs 30a to 30d, thereby controlling the light amount ratio of the LEDs 30a to 30d in each observation mode.

Figure 4:
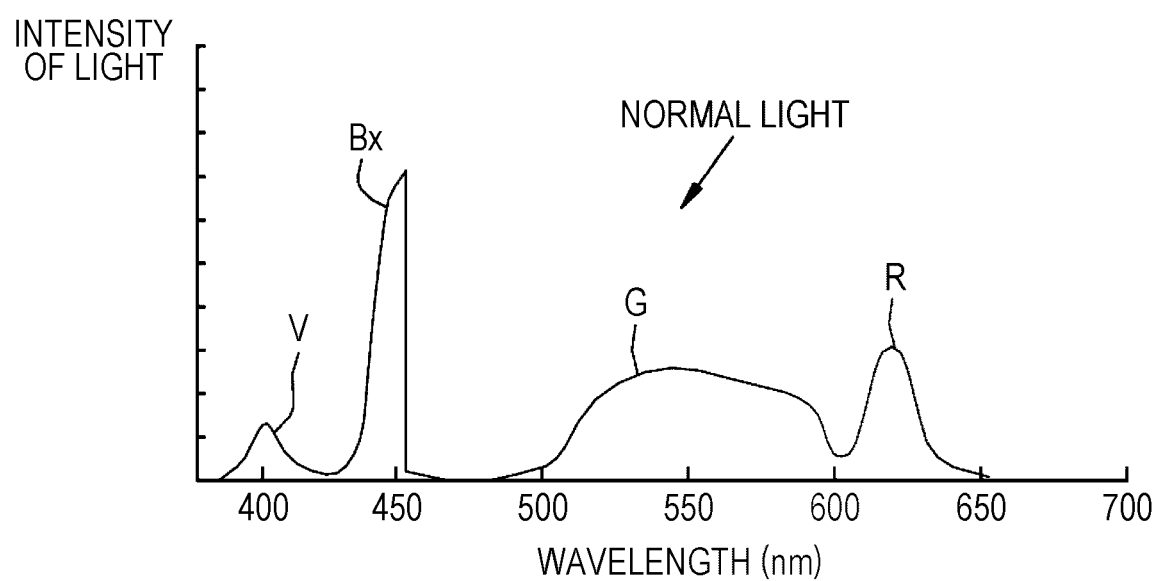
FIG. 4 is a graph illustrating a spectrum of normal light.

As illustrated in FIG. 4, in the normal mode, the light source control unit 32 turns on all the LEDs 30a to 30d. The light amount ratio among the violet light V, the blue light Bx, the green light G, and the red light R is set such that the peak intensity of the blue light Bx is higher than the peak intensities of the violet light V, the green light G, and the red light R. Accordingly, in the normal mode, the light source device 14 emits, as normal light, multicolor light including the violet light V, the blue light Bx, the green light G, and the red light R. The normal light has a certain intensity or more in the blue range to the red range and is thus substantially white.

Figure 5:
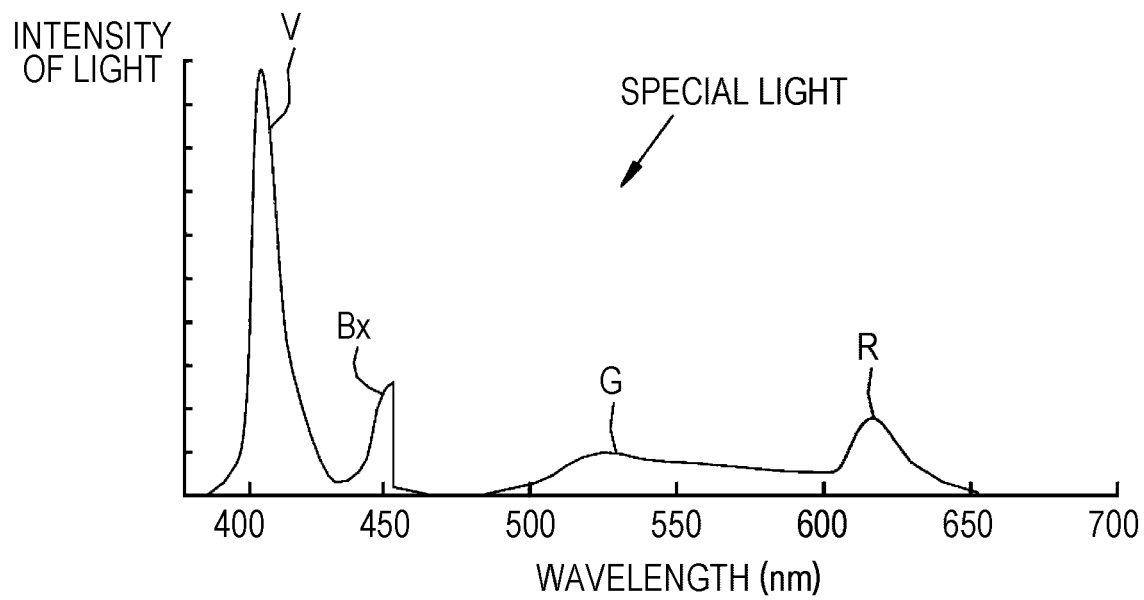
FIG. 5 is a graph illustrating a spectrum of special light.

As illustrated in FIG. 5, in the special mode, the light source control unit 32 turns on all the LEDs 30a to 30d. The light amount ratio among the violet light V, the blue light Bx, the green light G, and the red light R is set such that the peak intensity of the violet light V is higher than the peak intensities of the blue light Bx, the green light G, and the red light R and such that the peak intensities of the green light G and the red light R are lower than the peak intensities of the violet light V and the blue light Bx. Accordingly, in the special mode, multicolor light including the violet light V, the blue light Bx, the green light G, and the red light R and having a light amount ratio different from that in the normal mode is generated as special light. The special light has a large proportion of the violet light V and is thus bluish. The special light does not need to include light of all the four colors, and may include light from at least one of the LEDs 30a to 30d of four colors.

In the ROI search mode, the light source control unit 32 controls the light emission of each of the LEDs 30a to 30d in accordance with a light amount ratio input through the instruction input unit 19. For example, the light amount ratio of the normal mode, the light amount ratio of the special mode, and the like are input. Accordingly, normal light or special light is generated in the ROI search mode. In the ROI search mode, it is possible to alternately generate normal light and special light. In this case, a normal image and a special image are alternately acquired as endoscopic images.

In the ROI search mode, it is also possible to input a light amount ratio for acquiring hemoglobin oxygen saturation. In the case of acquiring hemoglobin oxygen saturation, the light source control unit 32 switches the illumination light for each imaging frame. Specifically, the B-LED 30b is turned on for a first imaging frame, and the B-LED 30b, the G-LED 30c, and the R-LED 30d are turned on for a second imaging frame subsequent to the first imaging frame. In addition, the light source control unit 32 controls the wavelength of light that the optical filter 30e passes, and changes the wavelength range of blue light to be generated every time the imaging frame is switched. In the first imaging frame, blue light in a narrow range, whose center wavelength and wavelength range are 470±10 nm, is generated. The center wavelength and wavelength range of the blue light generated in the first imaging frame are the center wavelength and wavelength range that cause the difference in light absorption coefficient between oxygenated hemoglobin and deoxygenated hemoglobin to be substantially the maximum in the blue wavelength range. In the second imaging frame, blue light in a wide range, whose center wavelength is about 450±10 nm and whose wavelength range is about 400 nm to 500 nm, is generated. With use of the individual types of illumination light, a lumen is illuminated, and oxygen saturation in the lumen is calculated based on the correlation between an endoscopic image acquired through image capturing and oxygen saturation. Accordingly, an image representing the oxygen saturation is acquired.

The illumination light emitted by the light source unit 30 enters the light guide 34 that extends through the insertion section 12a. The light guide 34 is built in the endoscope 12 and a universal cord, and causes the illumination light to propagate to the distal end portion 21 of the endoscope 12. The universal cord is a cord that connects the endoscope 12 to the light source device 14 and the processor device 16. A multimode fiber may be used as the light guide 34. As an example, a small-diameter fiber cable with a core diameter of 105 μm, a clad diameter of 125 μm, and a diameter including a protective layer serving as an outer cover of 0.3 to 0.5 mm may be used as the light guide 34.

The distal end portion 21 has an illumination optical system 36 and an imaging optical system 38. The illumination optical system 36 has an illumination lens 40. The illumination light that has propagated through the light guide 34 illuminates a lumen through the illumination lens 40. The imaging optical system 38 has an objective lens 42, a zoom lens 44, and an image sensor 46. Various types of light beams, such as reflected light from a mucous membrane or the like in a lumen, scattered light, and fluorescence, enter the image sensor 46 through the objective lens 42 and the zoom lens 44. The zoom lens 44 is freely adjusted between a telephoto end and a wide end by an operation of the zoom operation unit 28.

The image sensor 46 is a primary-color sensor and has three types of pixels: a B pixel (blue pixel) provided with a blue color filter, a G pixel (green pixel) provided with a green color filter, and an R pixel (red pixel) provided with a red color filter. Image capturing with the image sensor 46 in a lumen enables three types of endoscopic images to be acquired: a B image (blue image); a G image (green image); and an R image (red image).

A charge coupled device (CCD) image sensor, a complementary metal-oxide semiconductor (CMOS) image sensor, or the like can be used as the image sensor 46. The image sensor 46 is a primary-color sensor, but a complementary-color sensor may also be used. The complementary-color sensor has, for example, a cyan pixel provided with a cyan color filter, a magenta pixel provided with a magenta color filter, a yellow pixel provided with a yellow color filter, and a green pixel provided with a green color filter. The images of individual colors acquired when using the complementary-color sensor can be converted into a B image, a G image, and an R image similar to those in the case of using the primary-color sensor. Alternatively, a monochrome sensor that is not provided with color filters may be used instead of the image sensor 46.

The processor device 16 includes a controller 52, an endoscopic image acquisition unit 54, an image processing unit 60, a display control unit 68, and an insertion state acquisition unit 70.

The controller 52 has a central processing unit (CPU), a read only memory (ROM) that stores a control program and setting data that is necessary for control, a random access memory (RAM) serving as a work memory to which the control program is loaded, and the like. With the CPU executing the control program, the controller 52 controls the individual units of the processor device 16 and also controls the light source control unit 32 and the image sensor 46.

The endoscopic image acquisition unit 54 acquires a B image, a G image, and an R image as an endoscopic image from the image sensor 46. The endoscopic image acquisition unit 54 has a digital signal processor (DSP) 56 and a noise reduction unit 58, and performs various processing operations on the endoscopic image by using these devices.

The DSP 56 performs various signal processing operations, such as defect correction processing, offset processing, gain correction processing, linear matrix processing, gamma conversion processing, and demosaicing processing, on the endoscopic image. The defect correction processing corrects the pixel value of a defective pixel of the image sensor 46. The offset processing removes a dark current component from the image that has been subjected to the defect correction processing and sets an accurate zero level. The gain correction processing multiplies the image that has been subjected to the offset processing by a specific gain, thereby adjusting the signal level of each image.

The linear matrix processing increases the color reproducibility of the image that has been subjected to the gain correction processing. The gamma conversion processing adjusts the brightness and chroma of the image that has been subjected to the linear matrix processing. The demosaicing processing (also referred to as isotropic processing or synchronization processing) interpolates the pixel value of a missing pixel in the image that has been subjected to gamma conversion processing. The missing pixel means a pixel that does not have a pixel value because a pixel of another color is disposed there in the image sensor 46.

The noise reduction unit 58 performs noise reduction processing using, for example, a moving-average method, a median filter method, or the like, on the image that has been subjected to the demosaicing processing and so forth in the DSP 56, thereby reducing noise.

The image processing unit 60 acquires an endoscopic image from the endoscopic image acquisition unit 54 and performs predetermined image processing on the acquired endoscopic image, thereby generating a display image showing a lumen. The image processing unit 60 has a normal image processing unit 62, a special image processing unit 64, and a ROI searching image processing unit 66.

The normal image processing unit 62 operates in the normal mode and performs image processing operations, such as color conversion processing, color enhancement processing, and structure enhancement processing, on images of individual colors B, G, and R, thereby generating a normal image. In the color conversion processing, 3×3 matrix processing, gradation transformation processing, three-dimensional look-up table (LUT) processing, and the like are performed on the images of the individual colors B, G, and R. The color enhancement processing is processing of enhancing the color of the images, and the structure enhancement processing is processing of enhancing the structure of an observation target, for example, blood vessels or a pit pattern.

The special image processing unit 64 operates in the special mode and performs the above-described various image processing operations for emphasizing blood vessels, thereby generating a special image. In the special mode, the amount of light emitted by the V-LED 30a is large, and thus superficial blood vessels are emphasized in the special image.

The ROI searching image processing unit 66 operates in the ROI search mode, detects a ROI from an endoscopic image, and displays the position information of the detected ROI. In this embodiment, the position information of the ROI is displayed on the display unit 18 together with the endoscopic image. The details of the ROI searching image processing unit 66 will be described below with reference to another figure.

The display control unit 68 controls the display unit 18 to display a display image generated by the image processing unit 60. Accordingly, a normal image is displayed in the normal mode, a special image is displayed in the special mode, and an endoscopic image and the position information of a ROI are displayed in the ROI search mode.

The insertion state acquisition unit 70 acquires an insertion state of the endoscope 12 that is in a lumen. The insertion state acquisition unit 70 inputs the acquired insertion state of the endoscope 12 to the ROI searching image processing unit 66. In this embodiment, the insertion state acquisition unit 70 acquires an insertion state of the insertion section 12a, based on an insertion length of the insertion section 12a in a lumen.

Figure 6:
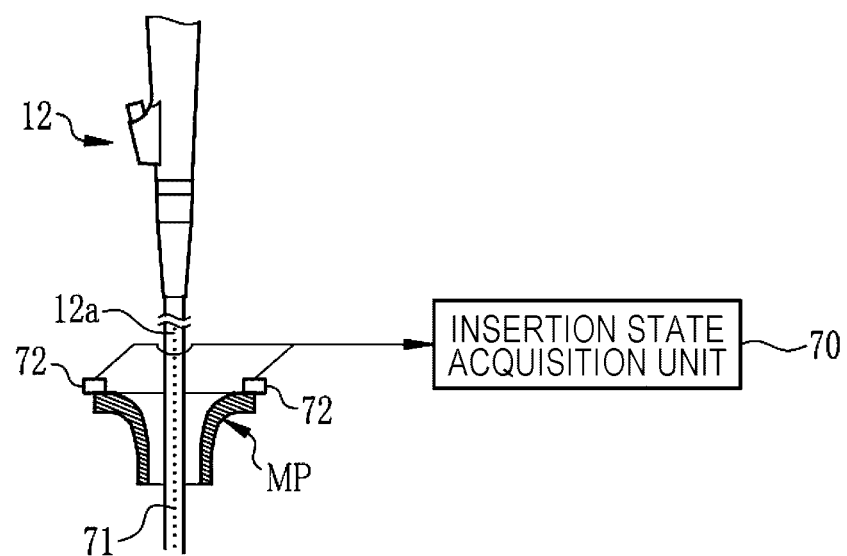
FIG. 6 is an explanatory diagram illustrating a method for acquiring an insertion length.

As illustrated in FIG. 6, measuring graduations 71 for measuring an insertion length of the insertion section 12a in a lumen are marked on the outer surface of the insertion section 12a of the endoscope 12. The measuring graduations 71 are constituted by points marked at a predetermined interval (for example, an interval of 1 cm) in the longitudinal direction of the insertion section 12a. A graduation detection sensor 72 for detecting the measuring graduations 71 is provided at the mouth (in the case of upper endoscopy) or the anus (in the case of lower endoscopy) of a patient. FIG. 6 illustrates that the graduation detection sensor 72 is provided on a mouthpiece MP held by the mouth of a patient. The graduation detection sensor 72 detects the measuring graduations 71 to acquire an insertion length of the insertion section 12a. In this way, in this embodiment, the measuring graduations 71 and the graduation detection sensor 72 constitute an insertion length acquisition unit. The graduation detection sensor 72 is connected to the processor device 16 in a wired or wireless manner, and transmits an insertion length of the insertion section 12a to the insertion state acquisition unit 70 of the processor device 16.

Figure 7:
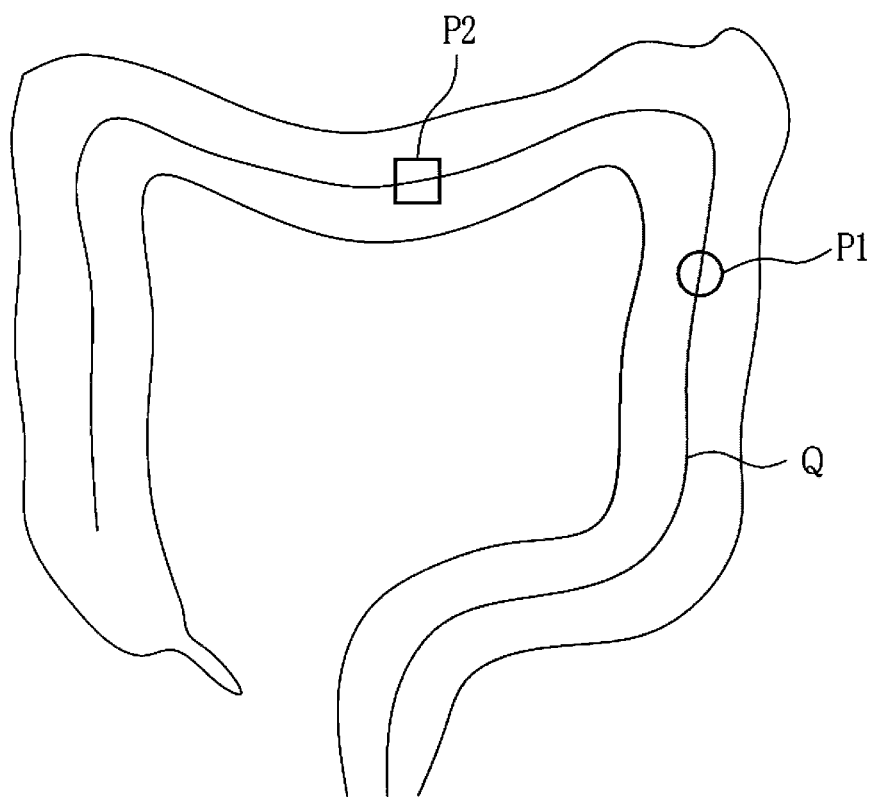
FIG. 7 is an explanatory diagram for describing a method for acquiring an insertion state of an insertion section of an endoscope.

As illustrated in FIG. 7, the insertion state acquisition unit 70 detects the position of the distal end portion 21 corresponding to the insertion length of the insertion section 12a in a diagnosis path Q along which the insertion section 12a is moved forward and backward in a lumen, thereby acquiring a detection position of the distal end portion 21. A detection position of the distal end portion 21 is acquired every time an insertion length of the insertion section 12a is measured. In FIG. 7, reference symbols P1 and P2 denote detection positions of the distal end portion 21. In this example, the detection position P2 of the distal end portion 21 is behind the detection position P1 of the distal end portion 21 in the lumen. That is, the insertion length at the detection position P2 is greater than the insertion length at the detection position P1.

In this embodiment, a detection position of the distal end portion 21 is acquired by using an insertion length of the insertion section 12a. Alternatively, for example, a magnetic sensor (not illustrated) may be provided on the insertion section 12a, and information acquired by the magnetic sensor may be used to acquire a detection position of the distal end portion 21, shape information of the insertion section 12a, and so forth. Alternatively, an X-ray image acquired by capturing an image of a subject using X rays may be used to acquire a detection position of the distal end portion 21.

Figure 8:
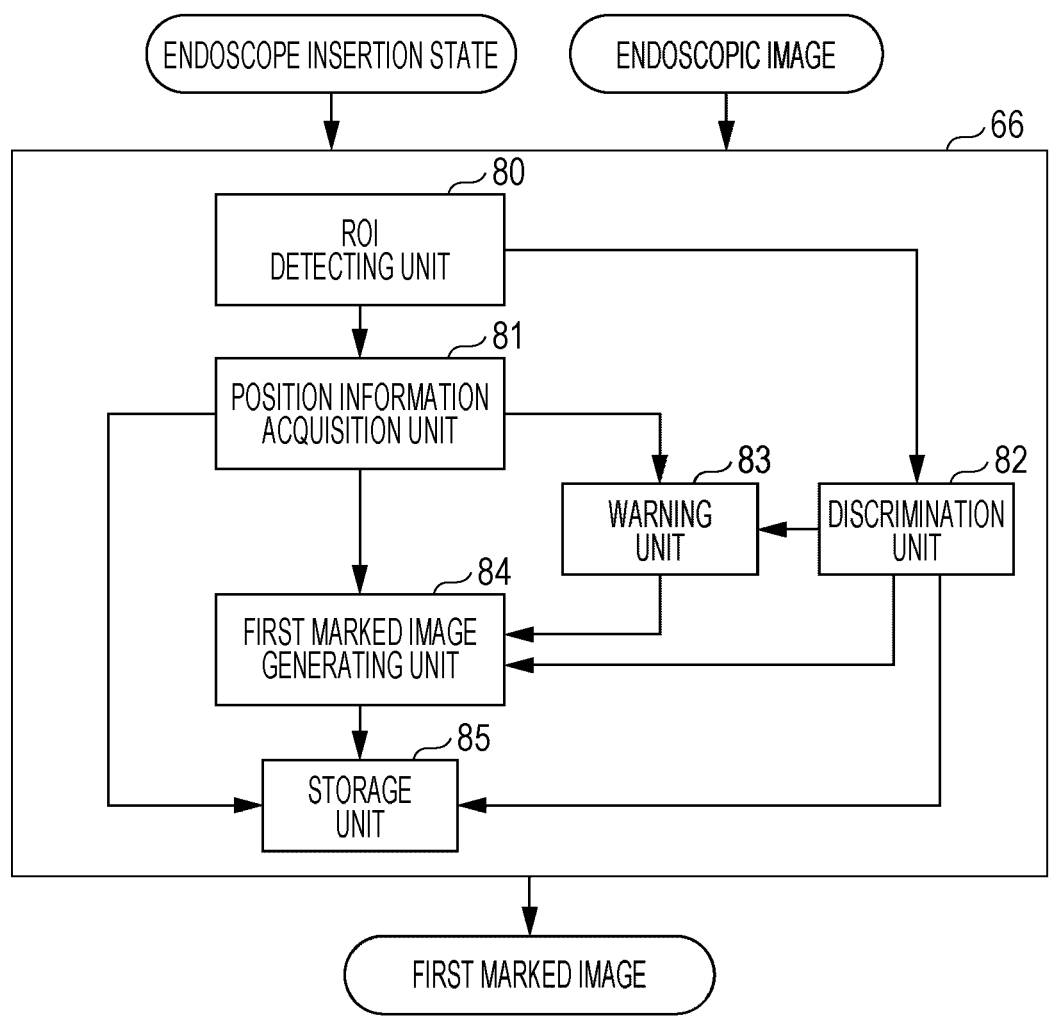
FIG. 8 is a block diagram illustrating the functions of a ROI searching image processing unit.

The ROI searching image processing unit 66 will be described. As illustrated in FIG. 8, the ROI searching image processing unit 66 has a ROI detecting unit 80, a position information acquisition unit 81, a discrimination unit 82, a warning unit 83, a first marked image generating unit 84, and a storage unit 85.

The ROI detecting unit 80 detects a ROI in a lumen by using an endoscopic image acquired from the endoscopic image acquisition unit 54. The ROI is a region including at least either a lesion portion or a normal portion in the lumen.

The ROI detecting unit 80 automatically performs processing of detecting a ROI from the endoscopic image. For example, the ROI detecting unit 80 stores in advance a plurality of template images of ROIs, and detects a region that matches a template image in the endoscopic image as a ROI. Here, "match" includes a case where the degrees of similarity of the regions compared to each other match, and also includes a case where the difference in the degree of similarity between the regions compared to each other is within a certain range. In this example, the ROI detecting unit 80 detects a ROI by using template matching. Alternatively, the ROI detecting unit 80 may detect a ROI by using, for example, deep learning, edge detection, texture analysis, or the like.

Figure 9:
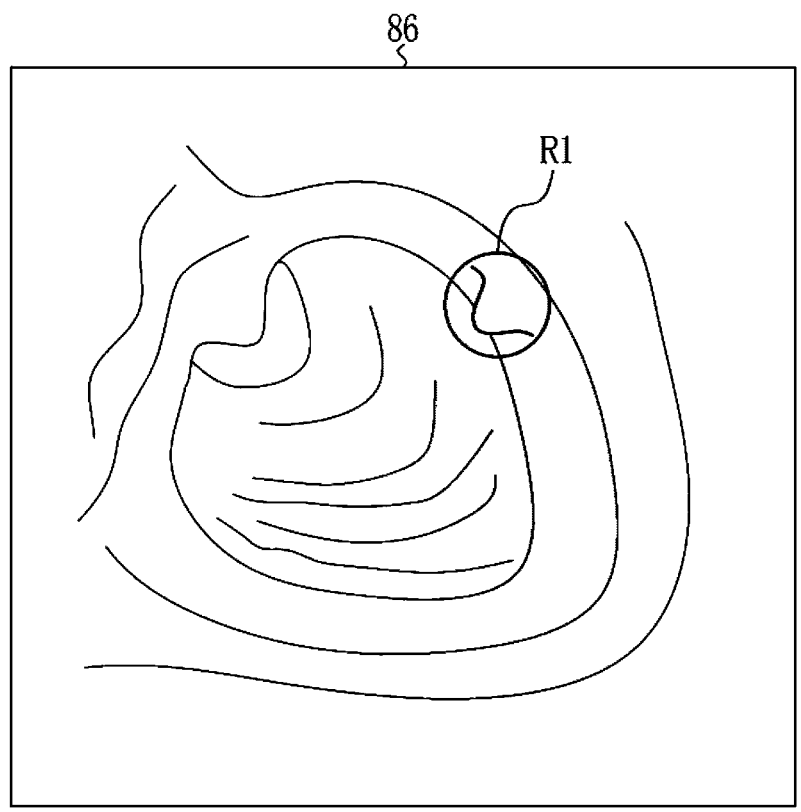
FIG. 9 is an explanatory diagram for describing detection of a ROI.
Figure 10:
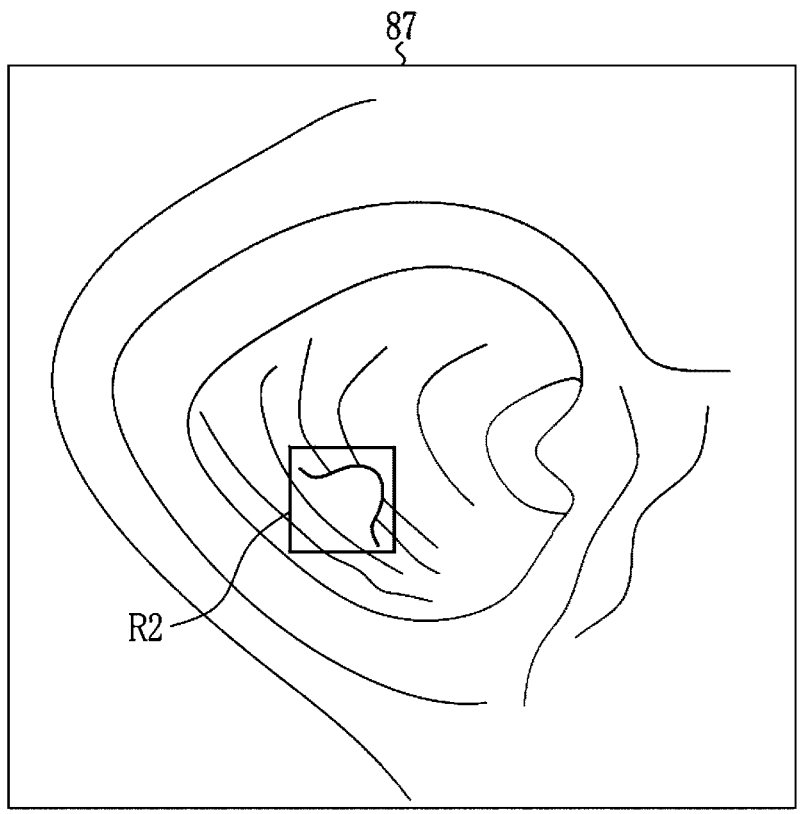
FIG. 10 is an explanatory diagram for describing detection of another ROI.

FIG. 9 illustrates a specific example of detecting a ROI from an endoscopic image 86 that is acquired at the detection position P1 of the distal end portion 21 in the lumen. FIG. 10 illustrates a specific example of detecting a ROI from an endoscopic image 87 that is acquired at the detection position P2 of the distal end portion 21 in the lumen. The ROI detecting unit 80 detects a ROI R1 from the endoscopic image 86 illustrated in FIG. 9, and detects a ROI R2 from the endoscopic image 87 illustrated in FIG. 10.

The position information acquisition unit 81 acquires the position information of the ROI detected by the ROI detecting unit 80. Specifically, the position information acquisition unit 81 acquires, as the position information of the ROI, the detection position of the distal end portion 21 at which the endoscopic image including the detected ROI is acquired. In this example, the detection position P1 of the distal end portion 21 is acquired as the position information of the ROI R1, and the detection position P2 of the distal end portion 21 is acquired as the position information of the ROI R2.

The discrimination unit 82 performs discrimination on the ROI detected by the ROI detecting unit 80. Specifically, the discrimination unit 82 at least performs discrimination to determine whether the ROI is a lesion portion or a normal portion, and outputs a discrimination result of the discrimination. In this embodiment, the discrimination unit 82 makes discrimination between a lesion portion and a normal portion, and also discriminates an adenoma (also referred to as a benign polyp). For example, regarding the ROI R1 in the endoscopic image 86 illustrated in FIG. 9, a discrimination result indicating an adenoma is acquired. Regarding the ROI R2 in the endoscopic image 87 illustrated in FIG. 10, a discrimination result indicating a lesion portion is acquired. Preferably, artificial intelligence (AI) is used as a discrimination method. Other than AI, deep learning, template matching, texture analysis, frequency analysis, or the like may be used as a discrimination method.

The discrimination unit 82 may discriminate the types of lesion portion. That is, a discrimination result output from the discrimination unit 82 may further indicate the type of lesion portion. The types of lesion portion depend on a portion on which a diagnosis is made. For example, in a diagnosis of the large intestine, the discrimination unit 82 determines the ROI to be a normal region, a hyperplastic polyp (HP), a sessile serrated adenoma/polyp (SSA/P), a traditional serrated adenoma (TSA), a laterally spreading tumor (LST), or a cancer. The types of lesion portion for which discrimination is to be performed may be set by, for example, input through the instruction input unit 19. The discrimination unit 82 may further perform discrimination of a position to be treated. That is, a discrimination result may further indicate a position to be treated.

The first marked image generating unit 84 generates a first marked image having a marking at the position corresponding to the position information of the ROI in a schematic diagram of the lumen. In this embodiment, the first marked image is displayed on the display unit 18, and thereby the position information of the ROI is displayed. The first marked image generating unit 84 stores in advance, as schematic diagrams of lumens, schematic diagrams of individual parts, such as the stomach, esophagus, and large intestine. The part for which the schematic diagram is to be used is set by, for example, input through the instruction input unit 19. In this embodiment, the schematic diagram of the large intestine is set.

Figure 11:
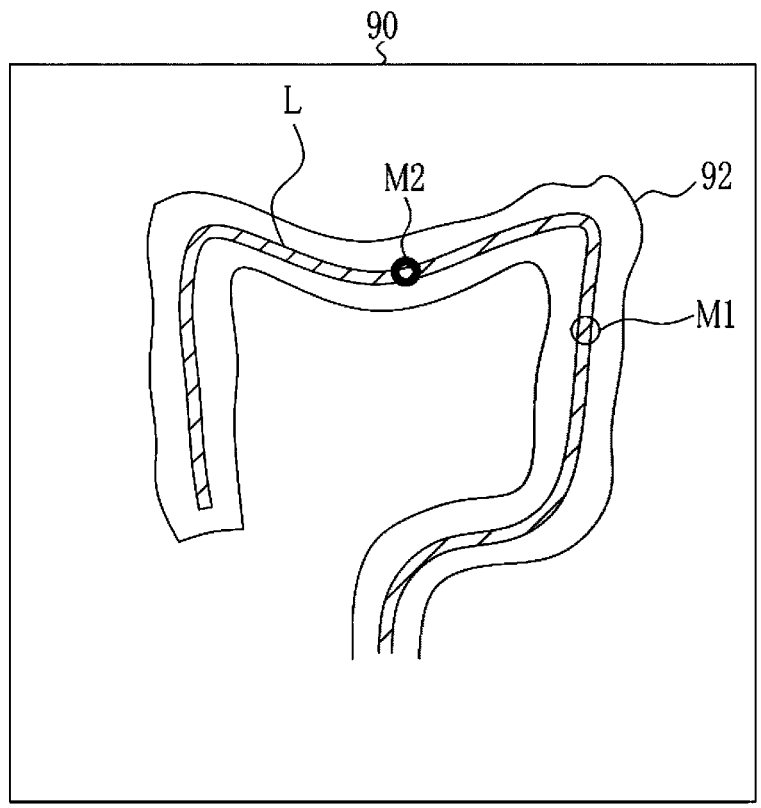
FIG. 11 is an explanatory diagram for describing a first marked image.

As illustrated in FIG. 11, in a first marked image 90, a mark M1 indicating that the ROI R1 has been detected is displayed in a superimposed manner at the position corresponding to the detection position P1 of the distal end portion 21 as the position information of the ROI R1, in a schematic diagram 92. Also, in the first marked image 90, a mark M2 indicating that the ROI R2 has been detected is displayed in a superimposed manner at the position corresponding to the detection position P2 of the distal end portion 21 as the position information of the ROI R2, in the schematic diagram 92. Accordingly, the user is able to recognize the positions of the ROIs. The marks M1 and M2 indicating that the ROIs have been detected are circular in FIG. 11. Alternatively, the marks M1 and M2 may be polygonal or the like.

The first marked image generating unit 84 causes the insertion state of the endoscope 12 acquired by the insertion state acquisition unit 70 to be displayed at the corresponding position in the schematic diagram 92. In FIG. 11, a reference symbol L denotes an insertion state of the endoscope 12. In this embodiment, the insertion state L of the endoscope 12 is represented with the length corresponding to the insertion length of the insertion section 12a. FIG. 11 illustrates the insertion state L of the endoscope 12 when the distal end portion 21 has reached the terminal of a forward-direction observation.

The first marked image generating unit 84 changes the display mode of the marking in accordance with a discrimination result acquired by the discrimination unit 82. A method of changing the color, size, thickness, shape, density, or the like of the marking may be used as a method for changing the display mode of the marking. In this example, the line thicknesses of the mark M1 representing an adenoma and the mark M2 representing a lesion portion are made different from each other so as to represent a difference in the discrimination result. In FIG. 11, the line of the mark M2 is thicker than the line of the mark M1. Preferably, a mark is displayed in yellow, red, or the like in the case of causing a user to recognize that the lesion needs a particular care.

The warning unit 83 outputs a warning, based on the position information of a ROI and the insertion state of the endoscope 12. Specifically, the warning unit 83 calculates the distance between the detection position of the distal end portion 21 as the position information of the ROI and the current detection position of the distal end portion 21, and generates a warning signal if the distance is smaller than or equal to a threshold value. In this embodiment, the warning unit 83 inputs the generated warning signal to the display control unit 68 so that a warning is displayed to indicate that the distal end portion 21 is close to the ROI. Characters, numerals, symbols, and the like may be used to display the warning. The warning is not limited to the one that is displayed. For example, the warning unit 83 may input a generated warning signal to a speaker (not illustrated) so that a warning sound is output from the speaker. Alternatively, vibration or flash light may be used.

The warning unit 83 changes a warning mode in accordance with a discrimination result acquired by the discrimination unit 82. In this example, the display mode of a warning is changed. For example, the display unit 18 is caused to display "!" when a discrimination result indicating an adenoma is acquired, whereas the display unit 18 is caused to display "!!" when a discrimination result indicating a lesion portion is acquired. Also in the case of outputting a warning sound as a warning, the warning mode may be changed in accordance with a discrimination result. Examples of a method for changing the warning mode of a warning sound include a method for changing the volume of the warning sound and a method for changing the pitch of the warning sound.

The storage unit 85 stores the position information of a ROI. In this embodiment, the storage unit 85 stores the position information and discrimination result of a ROI. That is, the storage unit 85 has a function as a ROI position information storage unit and a function as a ROI discrimination result storage unit. Preferably, the storage unit 85 stores the position information and discrimination result of the ROI in association with each other. The storage unit 85 may store either the position information or discrimination result of the ROI, or may store the position information of the ROI and the first marked image 90 in association with each other.

Figure 12:
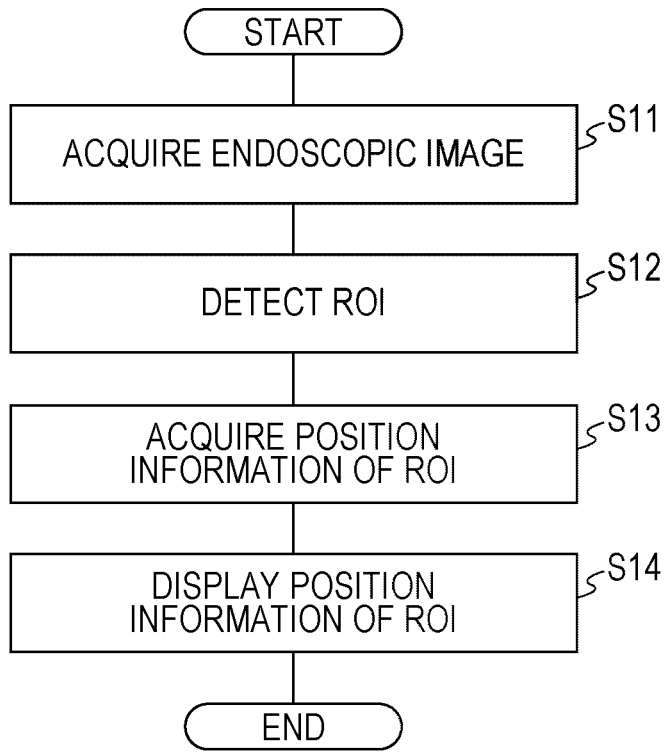
FIG. 12 is a flowchart for describing a series of steps in a ROI search mode.

Next, a series of steps in the ROI search mode will be described with reference to the flowchart in FIG. 12. In the ROI search mode, illumination light is generated in accordance with a light amount ratio input through the instruction input unit 19. The endoscope 12 captures an image of a lumen illuminated with the illumination light, thereby acquiring an endoscopic image. The endoscopic image is transmitted to the processor device 16. Accordingly, the endoscopic image acquisition unit 54 in the processor device 16 acquires the endoscopic image (step S11). The endoscopic image acquired by the endoscopic image acquisition unit 54 undergoes various processing operations and is then input to the ROI searching image processing unit 66.

In the ROI search mode, the insertion state acquisition unit 70 acquires an insertion state of the endoscope 12. The insertion state of the endoscope 12 is acquired based on an insertion length of the insertion section 12a in the lumen. The insertion length of the insertion section 12a is measured by the insertion length acquisition unit. The insertion length acquisition unit is constituted by the measuring graduations 71 and the graduation detection sensor 72 in this example. The graduation detection sensor 72 detects the measuring graduations 71, thereby acquiring the insertion length of the insertion section 12a. With use of the insertion length of the insertion section 12a, the insertion state acquisition unit 70 acquires a detection position of the distal end portion 21. The insertion state of the endoscope 12 acquired by the insertion state acquisition unit 70 is input to the ROI searching image processing unit 66.

In the ROI searching image processing unit 66, the ROI detecting unit 80 detects a ROI in the lumen by using the endoscopic image (step S12). The detection of a ROI is automatically performed every time an endoscopic image is acquired.

The position information acquisition unit 81 acquires the position information of the ROI detected by the ROI detecting unit 80 (step S13). In this example, the position information acquisition unit 81 acquires, as the position information of the ROI, the detection position of the distal end portion 21 at which the endoscopic image including the detected ROI is acquired.

The position information of the ROI acquired by the position information acquisition unit 81 is displayed on the display unit 18 (step S14). Accordingly, the user, such as a medical practitioner, is able to operate the endoscope 12 while viewing the position information of the ROI displayed on the display unit 18, and is thus able to easily re-search for the detected ROI. As a result, the diagnosis time taken to re-search for the detected ROIs R1 and R2 is shortened. The present invention is particularly effective in the case of re-searching for a ROI during a backward-direction observation in a diagnosis or in another facility.

The display of the position information of the ROI is performed by displaying, on the display unit 18, the first marked image 90 having a marking at the position corresponding to the position information of the ROI in the schematic diagram 92 of the lumen. The first marked image 90 is generated by the first marked image generating unit 84.

Figure 13:
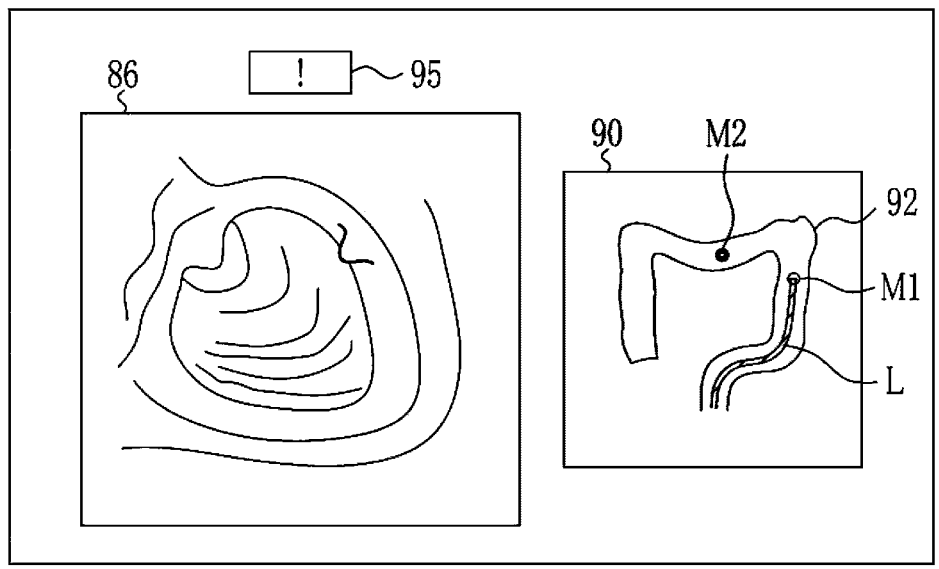
FIG. 13 is a diagram illustrating a display screen of a display unit that displays the first marked image.

For example, as illustrated in FIG. 13, the first marked image 90 is displayed on the display screen of the display unit 18. In FIG. 13, the endoscopic image 86 is displayed in addition to the first marked image 90. In the first marked image 90, the mark M1 indicating that the ROI R1 has been detected and the mark M2 indicating that the ROI R2 has been detected are displayed. Accordingly, the user is able to easily recognize the positions of the ROIs, and thus the diagnosis time taken to re-search for the ROIs R1 and R2 is further shortened.

In the first marked image 90, the insertion state L of the endoscope 12 is displayed at the corresponding position in the schematic diagram 92. In FIG. 13, the end of the insertion state L of the endoscope 12 is at the position of the mark M1. That is, it is indicated that the distal end portion 21 of the endoscope 12 in the lumen is at the detection position P1 at which the ROI R1 has been detected. Accordingly, the user is able to recognize the current insertion state of the endoscope 12, and is thus able to move the distal end portion 21 of the endoscope 12 to a desired position in a short time. As a result, the diagnosis time is further shortened.

The mark M1 and the mark M2 are displayed in different manners in accordance with a discrimination result acquired by the discrimination unit 82. In FIG. 13, the line of the mark M2 is thicker than the line of the mark M1. This enables the user to easily recognize the discrimination result.

On the display screen of the display unit 18, a warning indication 95 indicating that the distal end portion 21 is close to the ROI is displayed (see FIG. 13). Accordingly, the ROI is prevented from being overlooked.

The display mode of the warning indication 95 is changed in accordance with a discrimination result acquired by the discrimination unit 82. In FIG. 13, "!" is displayed as the warning indication 95 in a case where a discrimination result indicating an adenoma is acquired by the discrimination unit 82.

Figure 14:
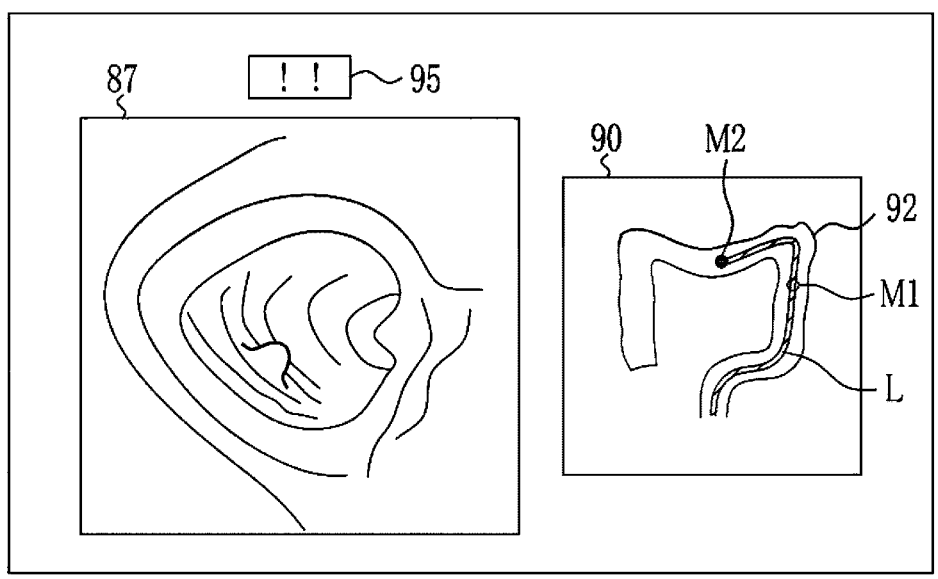
FIG. 14 is a diagram illustrating the display screen in which a warning indication has been changed in accordance with a discrimination result.

On the other hand, in a case where the end of the insertion state L of the endoscope 12 is at the position of the mark M2 as illustrated in FIG. 14, that is, in a case where the distal end portion 21 of the endoscope 12 in the lumen is at the detection position P2 at which the ROI R2 has been detected, the warning indication 95 is changed to "!!". Because the ROI R2 is a region for which a discrimination result indicating a lesion portion is acquired by the discrimination unit 82, it is preferable to display the warning indication 95 that is further emphasized. This enables the user to recognize that the lesion needs a particular care, which makes it possible to more reliably prevent the ROI requiring a detailed examination or treatment from being overlooked.

The position information of the ROI acquired by the position information acquisition unit 81 is stored in the storage unit 85 serving as the ROI position information storage unit. The position information of the ROI stored in the storage unit 85 is used, for example, at an endoscopic diagnosis in another facility. Accordingly, the diagnosis time taken to re-search for the ROI in the other facility is shortened more reliably.

The discrimination result output from the discrimination unit 82 is stored in the storage unit 85 serving as the discrimination result storage unit. Accordingly, the discrimination result can be used in, for example, another facility.

The method for displaying the position information of a ROI is not limited to the method for displaying the first marked image 90 as in this embodiment. For example, lumen portion information of a plurality of lumen portions, which are acquired by dividing a lumen, may be displayed as the position information of a ROI. For example, the large intestine is divided into the cecum, the ascending colon, the transverse colon, the descending colon, the sigmoid colon, and the rectum as lumen portions. The lumen portion information is, for example, the name of a lumen portion. The position information acquisition unit 81 specifies a lumen portion in which a ROI has been detected in the lumen, and acquires the lumen portion information of the specified lumen portion as the position information of the ROI. For example, the position information acquisition unit 81 specifies a lumen portion by using template matching, deep learning, edge detection, texture analysis, frequency analysis, or the like by using an endoscopic image. The method for specifying a lumen portion is not limited to the method of using an endoscopic image as described above. For example, a lumen portion may be specified by using the magnetic sensor, an X-ray image, the insertion length of the insertion section 12a, or the like. The lumen portion information acquired by the position information acquisition unit 81 is displayed on the display unit 18 as the position information of the ROI.

Figure 15:
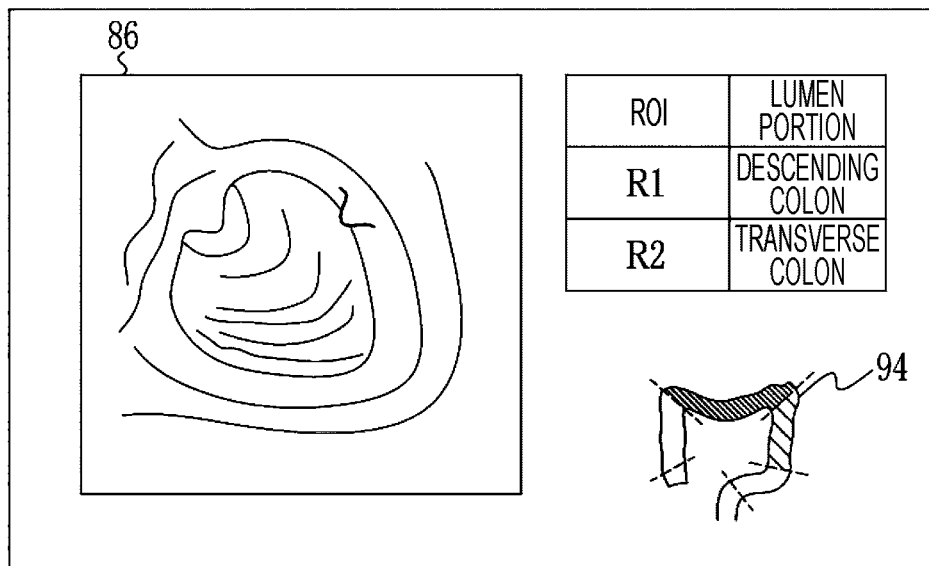
FIG. 15 is a diagram illustrating a display screen that displays lumen portion information as position information of ROIs.

FIG. 15 illustrates a specific example in which, in a case where the ROI R1 and the ROI R2 have been detected, the lumen portion information of the lumen portion in which the ROI R1 has been detected and the lumen portion information of the lumen portion in which the ROI R2 has been detected are displayed on the display screen of the display unit 18. In this example, the names of the lumen portions are displayed in text as the lumen portion information, and it is indicated that the ROI R1 has been detected in the descending colon and that the ROI R2 has been detected in the transverse colon.

In FIG. 15, a schematic diagram 94 of a lumen is displayed. The schematic diagram 94 is divided into six sections corresponding to the cecum, the ascending colon, the transverse colon, the descending colon, the sigmoid colon, and the rectum. In the schematic diagram 94, the section corresponding to the descending colon and the section corresponding to the transverse colon are displayed differently from the other sections. Furthermore, in FIG. 15, the difference between the section corresponding to the descending colon and the section corresponding to the transverse colon is represented by the difference in intervals of hatching. In this example, the schematic diagram 94 is also displayed on the display screen of the display unit 18, but the method for displaying the lumen portion information is not limited thereto. The display mode of the section in which a ROI has been detected may be changed in accordance with a discrimination result.

In addition, distance information indicating the distance from a reference structure included in the lumen may be displayed as the position information of a ROI. The reference structure is a characteristic structure, such as the Bauhin's valve (ileocecal valve), the anus, or "the x-th fold from the anus". The reference structure to be used is set by, for example, input through the instruction input unit 19. The reference structure to be used can be set for each ROI that has been detected. The reference structure is detected from an endoscopic image by, for example, the ROI detecting unit 80. For example, the Bauhin's valve is detected from an endoscopic image that is acquired when the distal end portion 21 reaches the terminal of a forward-direction observation. The anus may be detected based on the insertion length of the insertion section 12a. The method for detecting a reference structure is not limited to the method described above, for example, the reference structure may be detected by using the magnetic sensor, an X-ray image, and the like. The position information acquisition unit 81 acquires distance information indicating the distance from the reference structure in the ROI by using the detection position of the ROI and the detection position of the reference structure. The distance information acquired by the position information acquisition unit 81 is displayed on the display unit 18 as the position information of the ROI.

Figure 16:
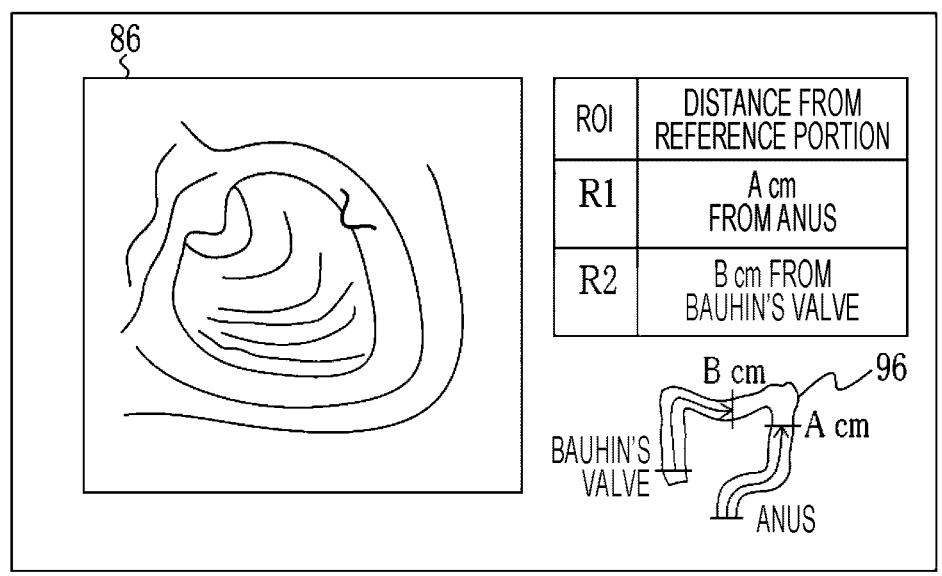
FIG. 16 is a diagram illustrating a display screen that displays distance information indicating the distance from a reference structure as position information of ROIs.

FIG. 16 illustrates a specific example in which, in a case where the ROI R1 and the ROI R2 have been detected, the position of the ROI R1 is displayed as the distance from the anus and the position of the ROI R2 is displayed as the distance from the Bauhin's valve, on the display screen of the display unit 18. In FIG. 16, the distance information is displayed in the form of text and numerical values, that is, "A cm from the anus" is displayed for the ROI R1 and "B cm from the Bauhin's valve" is displayed for the ROI R2. In FIG. 16, the distance information is displayed in the form of text and numerical values and also a schematic diagram 96 of the lumen is displayed, but the method for displaying distance information indicating the distance from the reference structure is not limited thereto.

Of the insertion lengths of the insertion section 12a acquired by the insertion length acquisition unit, the insertion length with which a ROI has been detected may be displayed on the display unit 18 as the position information of the ROI.

Figure 17:
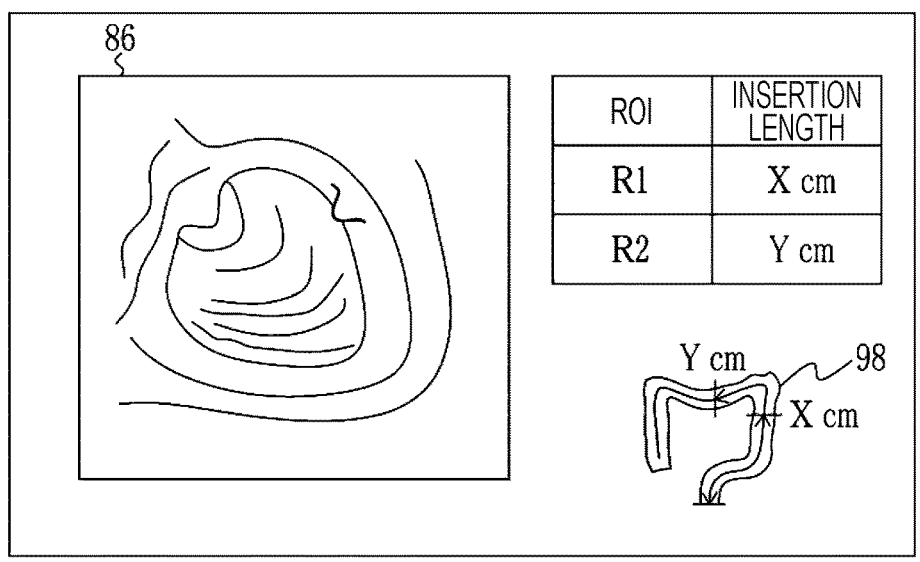
FIG. 17 is a diagram illustrating a display screen that displays insertion lengths as position information of ROIs.

FIG. 17 illustrates a specific example in which, in a case where the ROI R1 and the ROI R2 have been detected, the insertion length with which the ROI R1 has been detected and the insertion length with which the ROI R2 has been detected are displayed on the display screen of the display unit 18. In this example, the insertion lengths are displayed in the form of numerical values, that is, the insertion length with which the ROI R1 has been detected is X cm and the insertion length with which the ROI R2 has been detected is Y cm. In FIG. 17, the insertion lengths are displayed in the form of numerical values and also a schematic diagram 98 of the lumen is displayed, but the method for displaying the insertion lengths is not limited thereto.

In the above-described embodiment, the display mode of a marking is changed in accordance with a discrimination result acquired by the discrimination unit 82. Alternatively, a biological feature value of a ROI may be calculated from an endoscopic image, and the display mode of a marking may be changed by using the biological feature value in addition to the discrimination result acquired by the discrimination unit 82.

Figure 18:
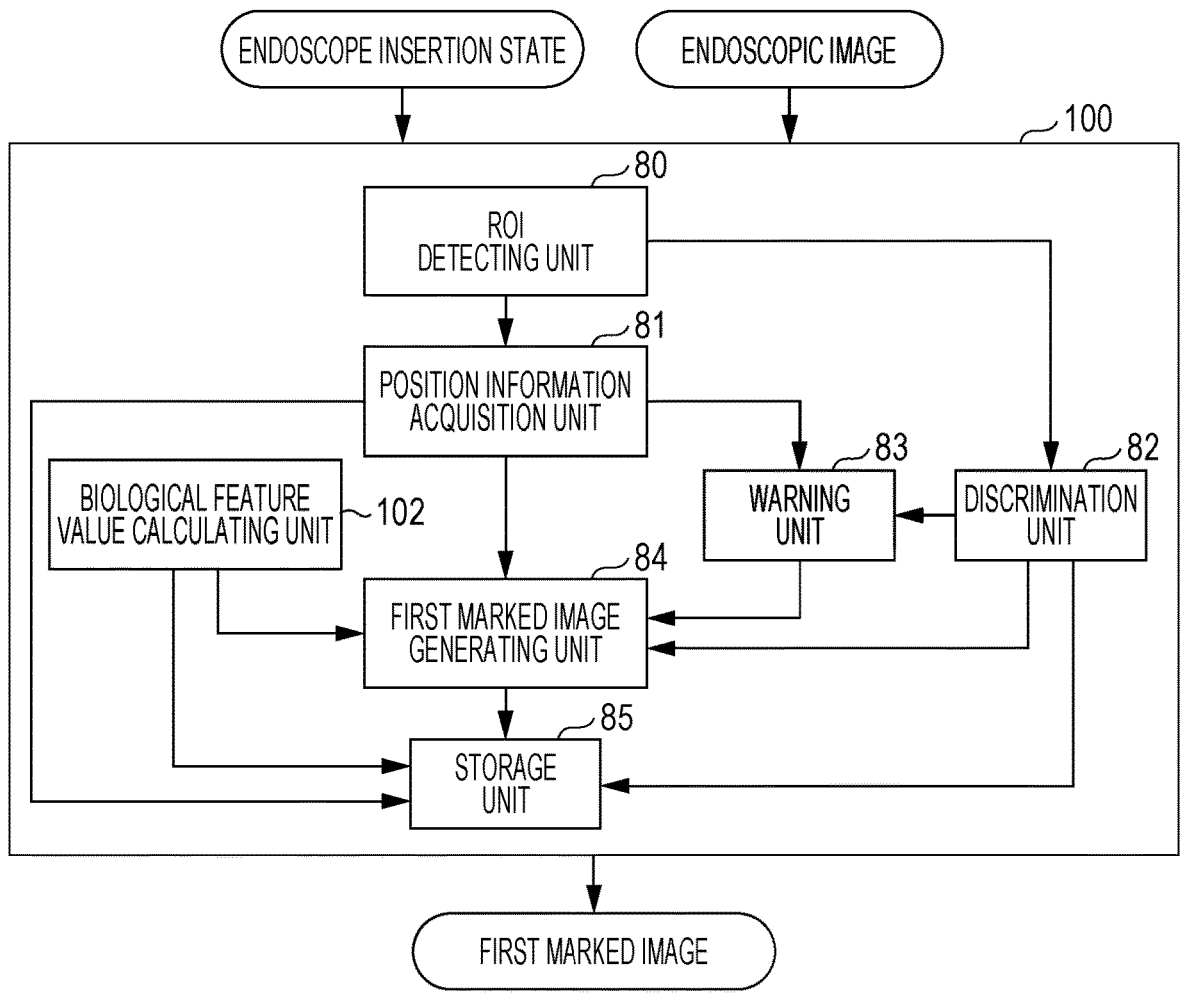
FIG. 18 is a block diagram illustrating the functions of a ROI searching image processing unit having a biological feature value calculating unit.

In this case, the ROI searching image processing unit 66 is replaced with a ROI searching image processing unit 100, as illustrated in FIG. 18. The ROI searching image processing unit 100 has a biological feature value calculating unit 102 in addition to the components of the ROI searching image processing unit 66. A description will not be given of the same components as those of the ROI searching image processing unit 66.

The biological feature value calculating unit 102 calculates a biological feature value from an endoscopic image. The calculation of the biological feature value uses an endoscopic image from which a ROI has been detected by the ROI detecting unit 80. The biological feature value is information indicating the property of blood vessels, and includes, for example, the number of blood vessels, the number of branches of blood vessels, the branch angles of blood vessels, the distance between branch points, the number of intersections of blood vessels, the thickness of a blood vessel, a change in the thickness of a blood vessel, the complexity of a change in the thickness of a blood vessel, the length of a blood vessel, the interval between blood vessels, the depth of a blood vessel, the height difference between blood vessels, the inclination of a blood vessel, the area of a blood vessel, the density of blood vessels, the contract of a blood vessel, the color of a blood vessel, a change in the color of a blood vessel, how much a blood vessel meanders, the blood concentration in a blood vessel, the oxygen saturation of a blood vessel, the proportion of arteries, the proportion of veins, the density of a pigment that has been given, a running pattern of blood vessels, the flow rate of blood in a blood vessel, and the like. The biological feature value calculating unit 102 calculates any one of these biological feature values. The types of biological feature values are not limited to the examples given above.

As a method for changing the display mode using a biological feature value, a method different from the method for changing the display mode using a discrimination result is used, for example. Specifically, in a case where the difference in the discrimination result is represented by the thickness of a marking as in the above-described embodiment, the biological feature value is represented by, for example, the color of the marking. Instead of differentiating the method for changing the display mode between the discrimination result and the biological feature value as described above, the thickness of a marking may be changed, for example, by using both the discrimination result and the biological feature value.

The biological feature value calculated by the biological feature value calculating unit 102 may be displayed on the display unit 18. In addition, the biological feature value may be stored in the storage unit 85 in association with the position information of the ROI.

In the above-described embodiment, the first marked image 90 having a marking at the position corresponding to the position information of the ROI in the schematic diagram 92 of the lumen is displayed on the display unit 18. Instead of this, a shape-of-inserted-endoscope image, representing the shape of the insertion section 12a in the lumen, may be acquired, and a second marked image having a marking at the position corresponding to the position information of the ROI in the shape-of-inserted-endoscope image may be displayed on the display unit 18.

Figure 19:
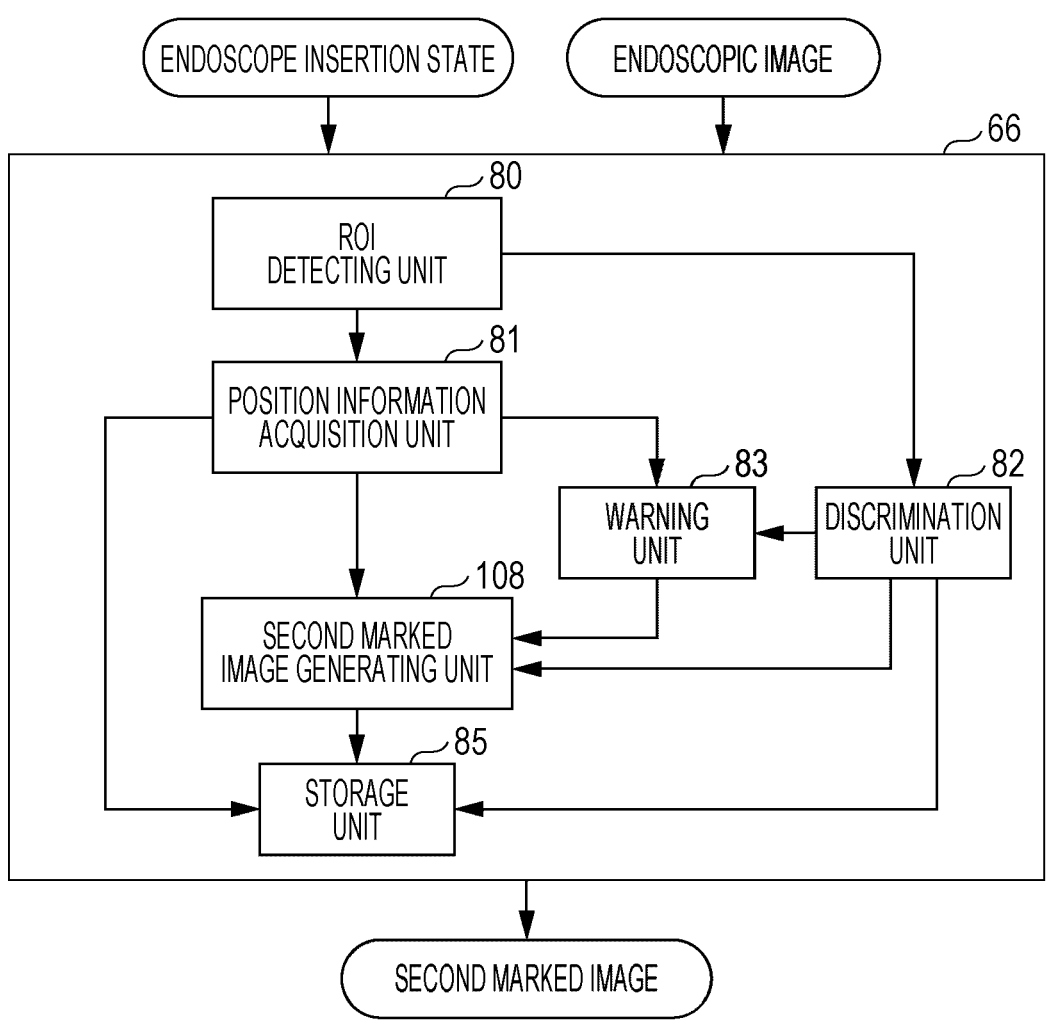
FIG. 19 is a block diagram illustrating the functions of a ROI searching image processing unit having a second marked image generating unit.

In this case, the first marked image generating unit 84 is replaced with a second marked image generating unit 108, as illustrated in FIG. 19. The insertion state acquisition unit 70 acquires the shape information of the insertion section 12a by using information acquired by the magnetic sensor (not illustrated) provided on the insertion section 12a. That is, the insertion state acquisition unit 70 functions as a shape-of-inserted-endoscope information acquisition unit that acquires the shape information of the insertion section 12a of the endoscope 12 that is in the lumen.

The second marked image generating unit 108 performs image processing by using the shape information of the insertion section 12a acquired by the insertion state acquisition unit 70 serving as the shape-of-inserted-endoscope information acquisition unit, thereby acquiring a shape-of-inserted-endoscope image. In the shape-of-inserted-endoscope image, the shape of the insertion section 12a is three-dimensionally expressed on the display screen of the display unit 18. The second marked image generating unit 108 generates a second marked image having a marking at the position corresponding to the position information of a ROI in the shape-of-inserted-endoscope image.

Figure 20:
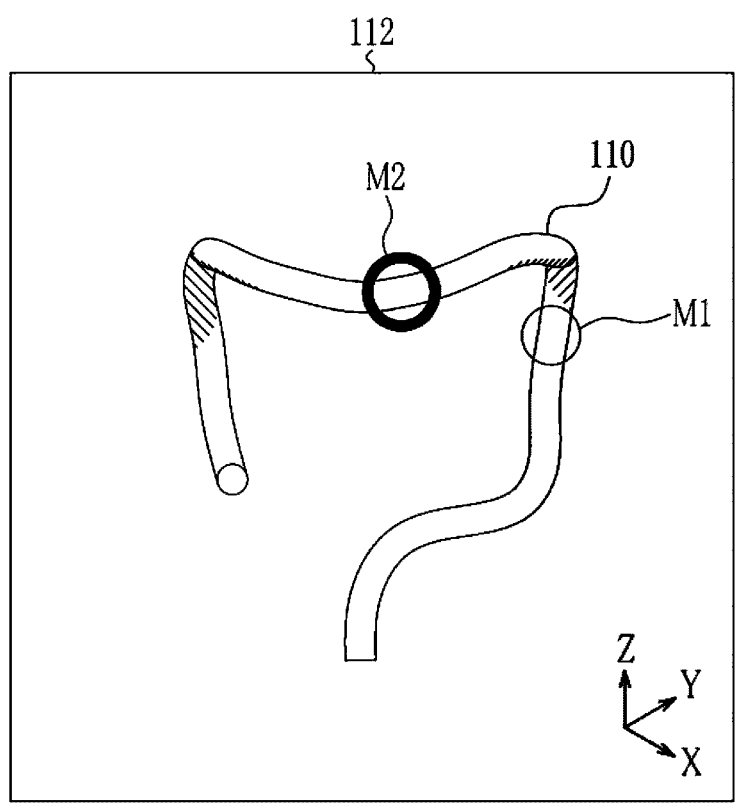
FIG. 20 is an explanatory diagram for describing a second marked image.

FIG. 20 illustrates a second marked image 112 in which, in a case where the ROI R1 and the ROI R2 have been detected, the mark M1 indicating that the ROI R1 has been detected and the mark M2 indicating that the ROI R2 has been detected are displayed on a shape-of-inserted-endoscope image 110. The shape-of-inserted-endoscope image 110 has a shape similar to that of the lumen in which the endoscope has been inserted. Thus, the shape-of-inserted-endoscope image 110 and the marks M1 and M2 enable the user to recognize the positions of the ROIs. As a result, the diagnosis time taken to re-search for the detected ROIs R1 and R2 is shortened.

The second marked image generating unit 108 may change the display mode of a marking in accordance with a discrimination result acquired by the discrimination unit 82. In addition, the second marked image generating unit 108 may change the display mode of a marking by using a biological feature value in addition to the discrimination result acquired by the discrimination unit 82.

The storage unit 85 may store the position information of the ROI and the second marked image 112 in association with each other.

In addition, the discrimination result acquired by the discrimination unit 82 may be displayed on the display unit 18. The above-described discrimination using AI or the like does not necessarily guarantee 100% accurate discrimination of a lesion. Thus, the discrimination unit 82 may further calculate confidence in the discrimination result and may display it on the display unit 18. That is, the discrimination result output from the discrimination unit 82 may further indicate confidence in the discrimination result. As an example of a method for calculating confidence, a description will be given of the case of calculating confidence in a discrimination result indicating a lesion portion. In this case, a plurality of template images serving as image information specific to a lesion portion are stored in advance in the discrimination unit 82, a portion that matches template images is detected from an endoscopic image, and the ratio of the number of matching template images to the total number of template images is calculated as confidence. The method for calculating confidence is not limited thereto. In addition, an "agreement button" for determining whether a medical practitioner agrees to the discrimination result may be displayed on the display unit 18, so that the medical practitioner is allowed to give final approval for the discrimination result. In this case, the "agreement button" is preferably operated by using the instruction input unit 19.

Second Embodiment

In a second embodiment, an observation target is illuminated by using a laser light source and a fluorescent body instead of the LEDs 30a to 30d of four colors according to the above-described first embodiment. Hereinafter, a description will be given of only a part different from that of the first embodiment, and a description will not be given of a part substantially the same as that of the first embodiment.

Figure 21:
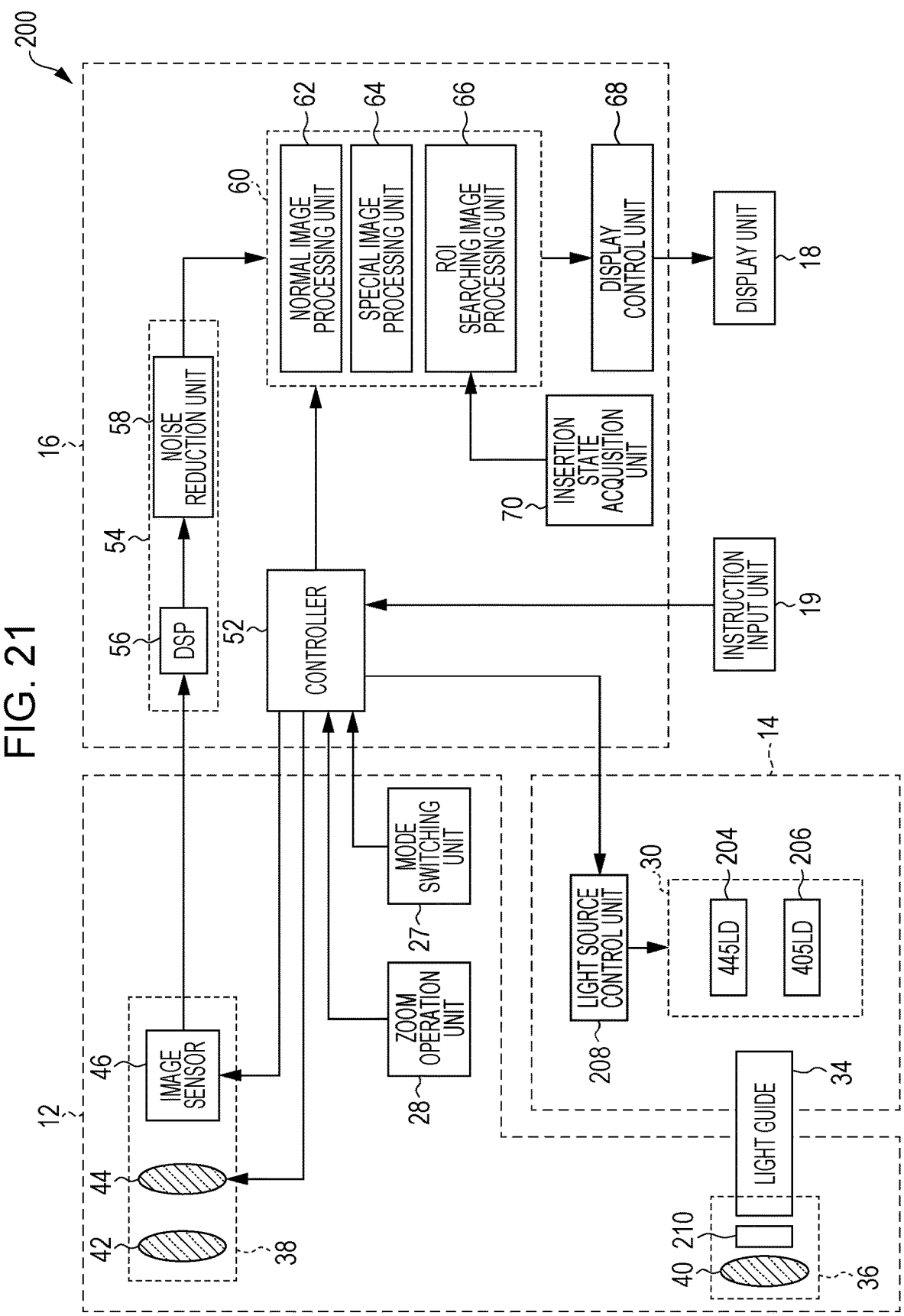
FIG. 21 is a block diagram illustrating the functions of an endoscope system according to a second embodiment.

As illustrated in FIG. 21, in an endoscope system 200 according to the second embodiment, the light source unit 30 of the light source device 14 is provided with, instead of the LEDs 30a to 30d of four colors, a blue laser light source (referred to as "445LD", LD stands for "laser diode") 204 that emits blue laser light having a center wavelength of 445±10 nm and a blue-violet laser light source (referred to as "405LD") 206 that emits blue-violet laser light having a center wavelength of 405±10 nm. The light emission from semiconductor light emitting elements of the light sources 204 and 206 is individually controlled by a light source control unit 208, and the light amount ratio between the light emitted by the blue laser light source 204 and the light emitted by the blue-violet laser light source 206 is freely changed.

In the normal mode, the light source control unit 208 turns on the blue laser light source 204. On the other hand, in the special mode, the light source control unit 208 turns on both the blue laser light source 204 and the blue-violet laser light source 206 and performs control so that the light emission rate of blue laser light is higher than the light emission rate of blue-violet laser light. In the ROI search mode, light is emitted in accordance with a light amount ratio input through the instruction input unit 19.

Preferably, the half-width of the blue laser light or the blue-violet laser light is about ±10 nm. As the blue laser light source 204 and the blue-violet laser light source 206, an InGaN-based laser diode of a broad area type can be used, and also an InGaNAs-based laser diode or a GaNAs-based laser diode can be used. Alternatively, a configuration using a light emitting body, such as a light emitting diode, may be used as the above-described light sources.

The illumination optical system 36 is provided with a fluorescent body 210 that the blue laser light or the blue-violet laser light from the light guide 34 enters, in addition to the illumination lens 40. The fluorescent body 210 is excited by the blue laser light and emits fluorescence. Part of the blue laser light passes through the fluorescent body 210 without exciting the fluorescent body 210. The blue-violet laser light passes through the fluorescent body 210 without exciting the fluorescent body 210. The light from the fluorescent body 210 illuminates a lumen through the illumination lens 40.

Figure 22:
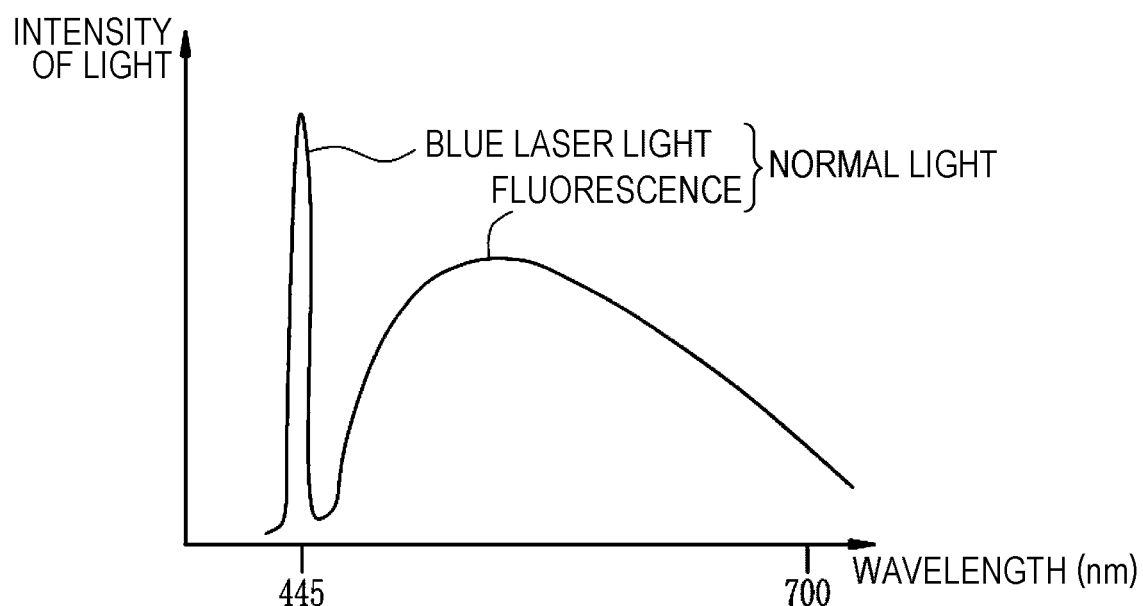
FIG. 22 is a graph illustrating a spectrum of normal light according to the second embodiment.

Here, in the normal mode, the blue laser light mainly enters the fluorescent body 210. As illustrated in FIG. 22, wide-range light for the normal mode, generated by combining the blue laser light and fluorescence emitted by the fluorescent body 210 as a result of excitation caused by the blue laser light, serves as normal light. The image sensor 46 captures an image of a lumen illuminated with the normal light, and accordingly a normal image is acquired.

Figure 23:
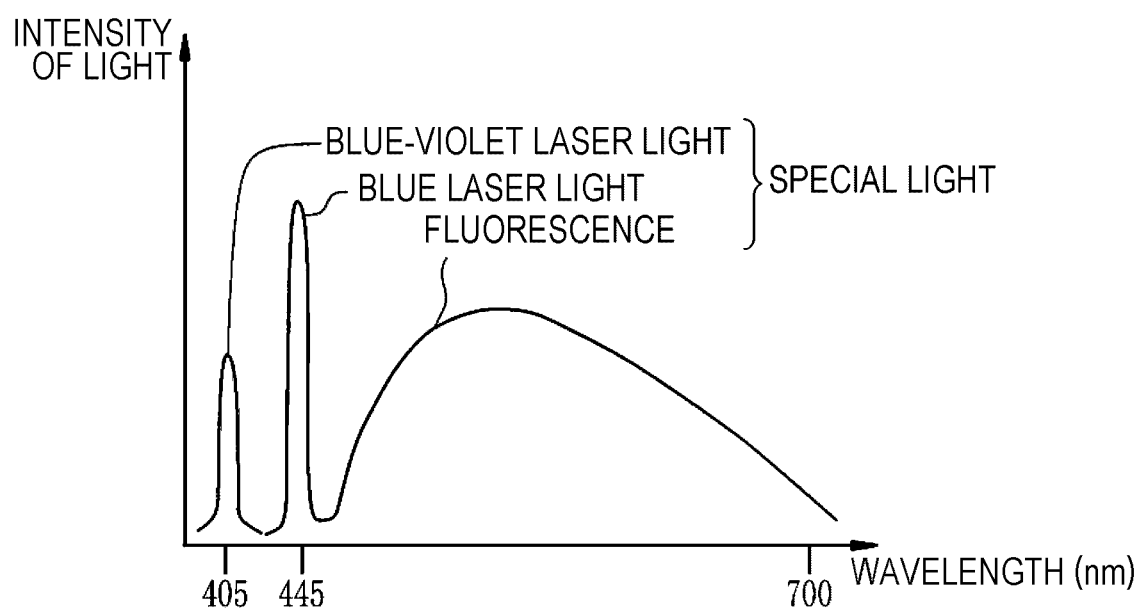
FIG. 23 is a graph illustrating a spectrum of special light according to the second embodiment.

On the other hand, in the special mode, both the blue-violet laser light and the blue laser light enter the fluorescent body 210. As illustrated in FIG. 23, wide-range light for the special mode, generated by combining the blue-violet laser light, the blue laser light, and fluorescence emitted by the fluorescent body 210 as a result of excitation caused by the blue laser light, serves as special light. The image sensor 46 captures an image of a lumen illuminated with the special light, and accordingly a special image is acquired.

In the ROI search mode, a lumen is illuminated with the illumination light emitted in accordance with a light amount ratio input through the instruction input unit 19. The image sensor 46 captures an image of the lumen illuminated with the illumination light, and accordingly an endoscopic image is acquired. Subsequently, the ROI detecting unit 80 detects a ROI in the lumen from the endoscopic image, and the position information acquisition unit 81 acquires the position information of the ROI. The acquired position information of the ROI is displayed on the display unit 18.

Preferably, the fluorescent body 210 is made of a plurality of types of fluorescent materials that absorb part of the blue laser light and emit green to yellow light as a result of excitation (for example, a YAG-based fluorescent body, a $BaMgAl_{10}O_{17}$ (BAM)-based fluorescent body, or the like). As in this configuration example, when a semiconductor light emitting element is used as an excitation light source of the fluorescent body 210, high-intensity white light can be acquired at high emission efficiency, the intensity of the white light can be easily adjusted, and a change in color temperature and chromaticity of the white light can be reduced.

Third Embodiment

In a third embodiment, an observation target is illuminated by using a white light source, such as a xenon lamp, and a rotational filter, instead of the LEDs 30a to 30d of four colors. Image capturing of the observation target may be performed by using a monochrome image sensor instead of the image sensor 46, which is a color image sensor. Hereinafter, a description will be given of only a part different from that of the first embodiment, and a description will not be given of a part substantially the same as that of the first embodiment.

Figure 24:
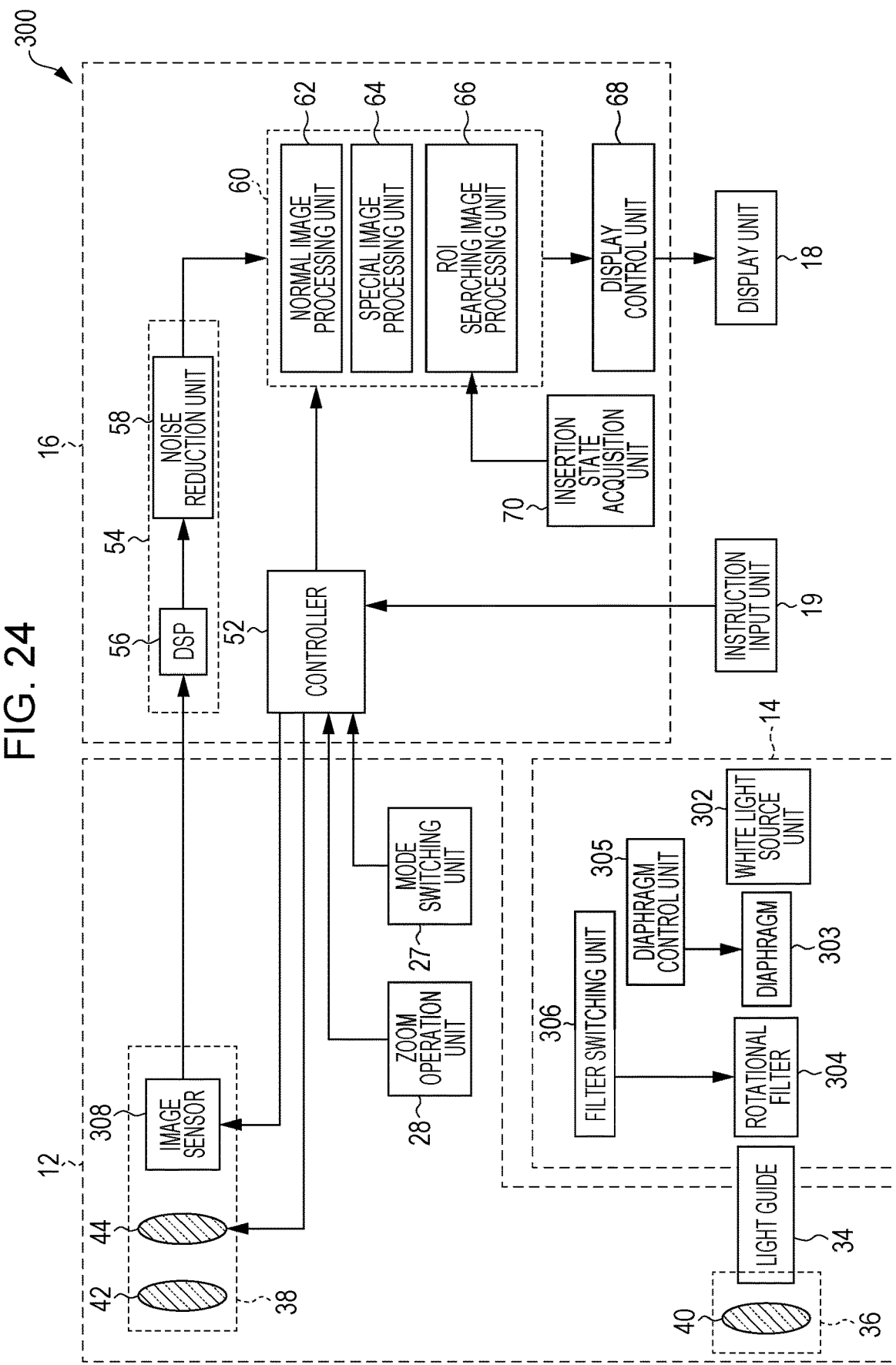
FIG. 24 is a block diagram illustrating the functions of an endoscope system according to a third embodiment.

In an endoscope system 300 illustrated in FIG. 24, the light source device 14 is provided with a white light source unit 302, a rotational filter 304, and a filter switching unit 306, instead of the LEDs 30a to 30d in the endoscope system 10. The imaging optical system 38 is provided with a monochrome image sensor 308 that is not provided with color filters, instead of the image sensor 46, which is a color image sensor. A diaphragm 303 is provided between the white light source unit 302 and the rotational filter 304. The area of the opening portion of the diaphragm 303 is adjusted by a diaphragm control unit 305.

The white light source unit 302 is a xenon lamp, a white LED, or the like, and emits white light having a wavelength range from blue to red. The rotational filter 304 includes a normal-mode filter 310 provided on the inner side closest to a rotational axis, and a special-mode filter 312 and a ROI-search-mode filter 314 that are provided on the outer side of the normal-mode filter 310 (see FIG. 25).

The filter switching unit 306 moves the rotational filter 304 in a diameter direction. Specifically, when the normal mode is set by the mode switching unit 27, the filter switching unit 306 inserts the normal-mode filter 310 into the light path of white light. When the special mode is set, the filter switching unit 306 inserts the special-mode filter 312 into the light path of white light. When the ROI search mode is set, the filter switching unit 306 inserts the ROI-search-mode filter 314 into the light path of white light.

Figure 25:
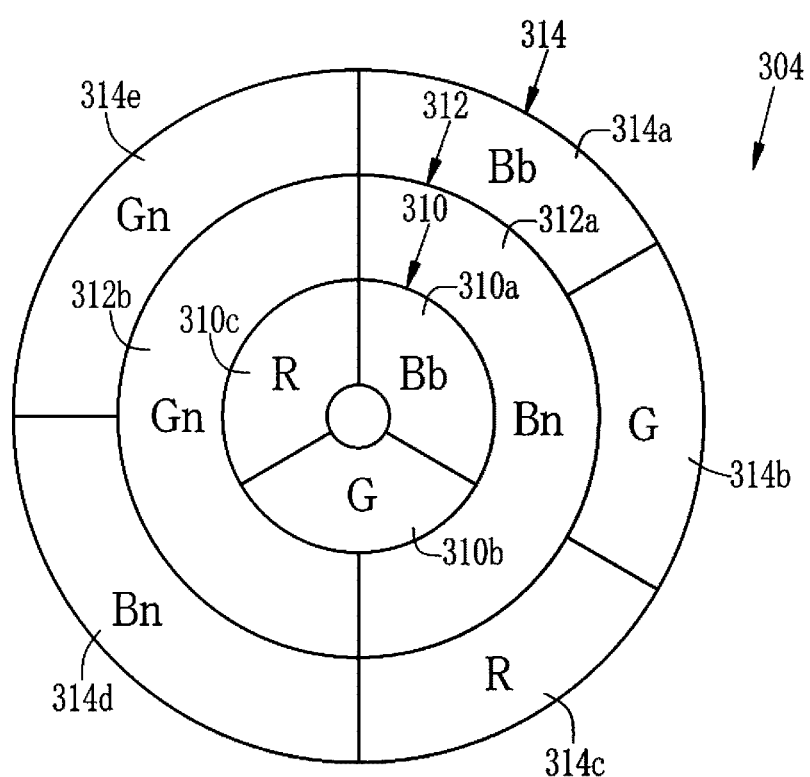
FIG. 25 is a plan view of a rotational filter.

As illustrated in FIG. 25, the normal-mode filter 310 is provided with a Bb filter 310a, a G filter 310b, and an R filter 310c in a circumferential direction. The Bb filter 310a passes wide-range blue light Bb having a wavelength range of 400 to 500 nm of white light. The G filter 310b passes green light G of white light. The R filter 310c passes red light R of white light. Thus, in the normal mode, rotation of the rotational filter 304 causes the wide-range blue light Bb, the green light G, and the red light R to be sequentially emitted as normal light toward an observation target.

The special-mode filter 312 is provided with a Bn filter 312a and a Gn filter 312b in the circumferential direction. The Bn filter 312a passes blue narrow-range light Bn in 400 to 450 nm of white light. The Gn filter 312b passes green narrow-range light Gn in 530 to 570 nm of white light. Thus, in the special mode, rotation of the rotational filter 304 causes the blue narrow-range light and the green narrow-range light to be sequentially emitted as special light toward an observation target.

The ROI-search-mode filter 314 is provided with a Bb filter 314a, a G filter 314b, an R filter 314c, a Bn filter 314d, and a Gn filter 314e in the circumferential direction in this example. The Bb filter 314a passes the wide-range blue light Bb of white light. The G filter 314b passes the green light G of white light. The R filter 314c passes the red light R of white light. The Bn filter 314d passes the blue narrow-range light Bn of white light. The Gn filter 314e passes the green narrow-range light Gn of white light. Thus, in the ROI search mode, rotation of the rotational filter 304 causes the wide-range blue light Bb, the green light G, and the red light R to be sequentially emitted as normal light toward an observation target, and the blue narrow-range light and the green narrow-range light to be sequentially emitted as special light toward the observation target.

In the endoscope system 300, in the normal mode, the monochrome image sensor 308 captures an image of a lumen every time the lumen is illuminated with the wide-range blue light Bb, the green light G, and the red light R. Accordingly, a Bc image signal is acquired during illumination with the wide-range blue light Bb, a Gc image signal is acquired during illumination with the green light G, and an Rc image signal is acquired during illumination with the red light R. The Bc image signal, the Gc image signal, and the Rc image signal constitute a normal image.

In the special mode, the monochrome image sensor 308 captures an image of a lumen every time the lumen is illuminated with the blue narrow-range light Bn and the green narrow-range light Gn. Accordingly, a Bn image signal is acquired during illumination with the blue narrow-range light Bn, and a Gn image signal is acquired during illumination with the green narrow-range light Gn. The Bn image signal and the Gn image signal constitute a special image.

In the ROI search mode, an endoscopic image is acquired based on the Bc image signal acquired during illumination with the wide-range blue light Bb, the Gc image signal acquired during illumination with the green light G, and the Rc image signal acquired during illumination with the red light R. In addition, an endoscopic image is acquired based on the Bn image signal acquired during illumination with the blue narrow-range light Bn and the Gn image signal acquired during illumination with the green narrow-range light Gn. Every time an endoscopic image is acquired, detection of a ROI is performed, and the position information of the ROI is acquired. The acquired position information of the ROI is displayed on the display unit 18.

REFERENCE SIGNS LIST 10 endoscope system
12 endoscope
12a insertion section
12b operation section
14 light source device
16 processor device
18 display unit
19 instruction input unit
21 distal end portion
22 bending portion
23 flexible pipe portion
25 angle knob
26 image storage operation unit
27 mode switching unit
28 zoom operation unit
30 light source unit
30a V-LED
30b B-LED
30c G-LED
30d R-LED
30e optical filter
32 light source control unit
34 light guide
36 illumination optical system
38 imaging optical system
40 illumination lens
42 objective lens
44 zoom lens
46 image sensor
52 controller
54 endoscopic image acquisition unit
56 DSP
58 noise reduction unit
60 image processing unit
62 normal image processing unit
64 special image processing unit
66 ROI searching image processing unit
68 display control unit
70 insertion state acquisition unit
71 measuring graduations
72 graduation detection sensor
80 ROI detecting unit
81 position information acquisition unit
82 discrimination unit
83 warning unit
84 first marked image generating unit
85 storage unit
86 endoscopic image
87 endoscopic image
90 first marked image
92, 94, 96, 98 schematic diagram
95 warning indication
100 ROI searching image processing unit
102 biological feature value calculating unit
108 second marked image generating unit
110 shape-of-inserted-endoscope image
112 second marked image
200 endoscope system according to second embodiment
204 blue laser light source
206 blue-violet laser light source
208 light source control unit
210 fluorescent body
300 endoscopy system
302 white light source unit
303 diaphragm
304 rotational filter
305 diaphragm control unit
306 filter switching unit
308 image sensor
310 normal-mode filter
310a Bb filter
310b G filter
310c R filter
312 special-mode filter
312a Bn filter
312b Gn filter
314 ROI-search-mode filter
314a Bb filter
314b G filter
314c R filter
314d Bn filter
314e Gn filter
B blue light
G green light
L insertion state of endoscope
M1 mark
M2 mark
P1 detection position of distal end portion
P2 detection position of distal end portion
Q diagnosis path
R red light
R1 ROI
R2 ROI
V violet light

What is claimed is:

1. An endoscope system comprising:
an endoscope; and
a processor configured to:
acquire an endoscopic image acquired by capturing an image of a lumen with the endoscope;
detect a region of interest in the lumen by using the endoscopic image;
acquire position information of the region of interest;
display the position information of the region of interest;
acquire shape information of an insertion section of the endoscope that is in the lumen;
acquire a shape-of-inserted-endoscope image by performing image processing using the shape information of the insertion section and generate a second marked image having a marking at a position corresponding to the position information of the region of interest in the shape-of-inserted-endoscope image; and
display the second marked image.

2. The endoscope system according to claim 1,
wherein the processor is further configured to:
generate a first marked image having a marking at a position corresponding to the position information of the region of interest in a schematic diagram of the lumen, and
display the first marked image.

3. The endoscope system according to claim 2,
wherein the processor is further configured to:
acquire an insertion state of the endoscope that is in the lumen, and
display the insertion state of the endoscope at a corresponding position of the schematic diagram.

4. The endoscope system according to claim 3,
wherein the processor is further configured to perform discrimination on the region of interest.

5. The endoscope system according to claim 4, wherein the processor is further configured to output a discrimination result at least indicating whether the region of interest is a lesion portion or a normal portion.

6. The endoscope system according to claim 5, wherein the discrimination result further indicates a type of lesion portion.

7. The endoscope system according to claim 5, wherein the discrimination result further indicates confidence in the discrimination result.

8. The endoscope system according to claim 6, wherein the discrimination result further indicates confidence in the discrimination result.

9. The endoscope system according to claim 5, further comprising a storage that stores the discrimination result.

10. The endoscope system according to claim 6, further comprising a storage that stores the discrimination result.

11. The endoscope system according to claim 4, wherein the processor is further configured to change a display mode of the marking in accordance with a discrimination result.

12. The endoscope system according to claim 4, wherein the processor is further configured to provide a warning, based on the position information of the region of interest and the insertion state of the endoscope.

13. The endoscope system according to claim 12, wherein the processor is further configured to change a warning mode in accordance with a discrimination result.

14. The endoscope system according to claim 4,
wherein the processor is further configured to:
calculate a biological feature value of the region of interest, and
change a display mode of the marking by using the biological feature value in addition to a discrimination result.

15. The endoscope system according to claim 1, wherein the lumen is divided into a plurality of lumen portions,
the position information of the region of interest is lumen portion information of a lumen portion in which the region of interest has been detected among the plurality of lumen portions, and
the processor is further configured to display the lumen portion information as the position information of the region of interest.

16. The endoscope system according to claim 1, wherein
the position information of the region of interest is distance information indicating a distance from a reference structure in the lumen, and
the processor is further configured to display the distance information as the position information of the region of interest.

17. The endoscope system according to claim 1,
wherein the processor is further configured to:
acquire one or more insertion lengths of an insertion section of the endoscope in the lumen, and
display, as the position information of the region of interest, an insertion length with which the region of interest has been detected among the one or more insertion lengths.

18. The endoscope system according to claim 1, comprising:
a storage that stores the position information of the region of interest.

19. An operation method for an endoscope system, comprising:
acquiring an endoscopic image acquired by capturing an image of a lumen with an endoscope;
detecting a region of interest in the lumen by using the endoscopic image;
acquiring position information of the region of interest;
displaying the position information of the region of interest;
acquiring shape information of an insertion section of the endoscope that is in the lumen;
acquiring a shape-of-inserted-endoscope image by performing image processing using the shape information of the insertion section and generating a second marked image having a marking at a position corresponding to the position information of the region of interest in the shape-of-inserted-endoscope image; and
displaying the second marked image.

* * * * *